US006982313B2

(12) United States Patent
Roninson et al.

(10) Patent No.: US 6,982,313 B2
(45) Date of Patent: Jan. 3, 2006

(54) GENES AND GENETIC ELEMENTS ASSOCIATED WITH SENSITIVITY TO CHEMOTHERAPEUTIC DRUGS

(75) Inventors: Igor B. Roninson, Wilmette, IL (US); Andrei Gudkov, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 341 days.

(21) Appl. No.: 10/010,167

(22) Filed: Dec. 10, 2001

(65) Prior Publication Data
US 2004/0092729 A1 May 13, 2004

Related U.S. Application Data

(60) Division of application No. 09/568,315, filed on May 9, 2000, now Pat. No. 6,326,488, which is a division of application No. 08/929,208, filed on Sep. 9, 1997, now Pat. No. 6,060,244, which is a division of application No. 08/480,552, filed on Jun. 7, 1995, now Pat. No. 5,665,550, which is a continuation of application No. 08/033,086, filed on Mar. 9, 1993, now abandoned, which is a continuation-in-part of application No. PCT/US91/07492, filed on Oct. 11, 1991, which is a continuation-in-part of application No. 07/599,730, filed on Oct. 19, 1990, now Pat. No. 5,217,889.

(51) Int. Cl.
*C07K 7/04* (2006.01)

(52) U.S. Cl. .................................... 530/300; 530/329

(58) Field of Classification Search .............. 530/300, 530/329

See application file for complete search history.

(56) References Cited

U.S. PATENT DOCUMENTS

| | | | |
|---|---|---|---|
| 5,217,889 A | 6/1993 | Roninson | |
| 6,060,244 A | 5/2000 | Roninson | |
| 6,083,745 A | 7/2000 | Gudkov et al. | |
| 6,197,521 B1 | 3/2001 | Gudkov et al. | |
| 6,541,603 B1 * | 4/2003 | Kirschling et al. | ......... 530/300 |

FOREIGN PATENT DOCUMENTS

WO    WO 91/07492    5/1991

OTHER PUBLICATIONS

Albritton et al., "A Putative Murine Ecotropic Retrovirus Receptor Gene Encodes a Multiple Membrane–Spanning Protein and Confers Susceptibility to Virus Infection", 1989, Cell 57:659–666.
Altshul et al., "Basic Local Alignment Search Tool", 1990, J. Mol. Biol. 215:403–410.
Baim et al., "A Chimeric Mammalian Transactivator Based on the Lac Repressor that is regulated by Temperature and isopropyl b–D–thiogalactopyranoside", Proc Natl Acad Sci USA 88:5072–5076 (1991).

Baird et al., "Identification, Cloning and Characterization of the *Escherichia coli* sohA Gene, A Suppressor of the htrA (degP) Null Phenotype", J. Bacteriol 172: 1587–1594 (1990).
Ballester et al., "The NF1 Locus Encodes a Protein Funcationally Related to Mammalian GAP and Yeast IRA Proteins", 1990, Cell 62: 851–859.
Baltimore, "Intracellular Immunization", Nature 335: 395–396 (1988).
Barbacid, "ras GENES[1]" 1987, Ann. Rev. Biochem. 56: 779–827.
Bender et al., "Evidence that the Packaging Signal of Moloney Murine Leukemia Virus Extends into the gag Region", 1987, J. Virol 61: 1639–1646.
Bodine et al., "Development of a high–titer retrovirus producer cell line capable of gene transfer into rhesus monkey hematopoietic stem cells", Proc Natl Acad Sci USA 87:3738–3742 (1990).
Buchberg et al., "Sequence homology shared by neurofibromatosis type–1 gene and IRA–a and IRA–2 negative regulators of the RAS cyclic AMP pathway", 1990, Nature 347:291–294.
Bunnell et al., "A Dominant Negative Mutation in Two Proteins Created by Ectopic Expression of an AU–Rich 3' Untranslated Region", Somat. Cell Mol. Genet. 16: 151–162 (1990).
Call et al., "Isolation and Characterization of a Zinc Finger Polypeptide Gene at the Human Chromosome 11 Wilms' Tumor Locus", 1990, Cell 60: 509–520.
Ch'ng et al., "Antisense RNA complementary to 3' Coding and noncoding sequences of creatine kinase is a potent inhibitor of translation in vivo", Proc. Natl. Acad. Sci. 86: 10006–10010 (1989).
Chejanovsky et al., MutationJ. Virol. 64: 1764–1770 (1990).
Chen et al. "Internal Duplication and Homology with Bacterial Transport Proteins in the mdr1 (P–Glycoprotein) Gene from Multidrug–Resistant Human Cells" 47:381–389 (1986).
Culver et al. "In Vivo Gene Transfer with Retriviral Vector–Producer Cells for Treatment of Experimental Brain Tumors", Science 256:1550–1552 (1992).
Damm et al., "A Single Point Mutation in erbA restores the erythroid transforming potential of a mutant avian erythroblastosis virus (AEV) defective in both erbA and erbB oncogenes", 1987, EMBO J. 6: 375–382.

(Continued)

*Primary Examiner*—James Ketter
(74) *Attorney, Agent, or Firm*—McDonnell Boehnen Hulbert & Berghoff LLP

(57) ABSTRACT

The invention provides genetic suppressor elements that confer upon a cell resistance to one or more chemotherapeutic drug, methods for identifying and obtaining such elements, and methods of using such elements. The invention also provides cloned genes associated with sensitivity to chemotherapeutic drugs.

2 Claims, 42 Drawing Sheets

OTHER PUBLICATIONS

Damm et al., "Protein encoded by v–erbA functions as a thyroid–hormone receptor antagonist", Nature, vol. 339, Jun. 22, 1989 pp. 593–597.

Daugherty et al., "Antisense RNA: Effect of Ribosome Binding Sites, Target Location, Size, and Concentration on the Translation of Specific mRNA Molecules", Gene Anal. Tech. 6:1–16 (1989).

Deiss et al., "A Genetic Tool Uses to Identify Thioredoxin as a Mediator of a Growth Inhibitory Signal", Science vol. 252:117–120 (1991).

Duerre et al., "Effect of Methylation inhibitors on Gene Expression in HL–60 Cells", 1992, Biochem. Biolog. Cell. 70:703–711.

Eliyahu et al., "Participation of p53 Cellular Tumour Antigen in Transformation of Normal Embryonic Cells", 1984, Nature 312: 646–659.

Endow, The Emerging Kinesin Family of Microtubule Motor ProteinTrends Biochem Scie 16: 221–225 (1991).

Fearon et al., "Identification of a Chromosone 19q Gene That is Altered in Colorectal Cancers", 1990, Science 247: 49–56.

Fereira et al., "Suppression of Kinesin Expression in Cultured Hippocampal Neurons Using Antisense Oligonucleotides", J. Cell Biol 117:595–606 (1992).

Fields et al., "Presence of a Potent Transcription Activating Sequence in the p53 Protein", 1990 Science, 249:1046–1049.

Finlay et al., "Activating Mutations for Transformation by p53 Produce a Gene Product That Forms an hsc70–p53 Complex with an Altered Half–Life", 1988, Molec. Cell Biol. 8: 531–539.

Friedman et al., "Expression of a truncated viral trans–activator selectively impedes lytic infection by its cognate virus", 335:452–454 (1988).

Friend et al., "Deletions of a DNA sequence in retinoblastomas and mesenchymal tumors: Organization of the sequence and its encoded protein", 1987, Proc. Natl. Acad. Sci. USA 84:9059–9063.

Gessler et al., "Homozygous deletion in Wilms tumours of a zinc–finger gene identified by chromosome jumping", 1990, Nature 343: 774–778.

Graf & Beug, "Role of the v–erbA and v–erB Oncogenes of Avian Erythroblastosis Virus in Erythroid Cell Transformation", 1983, Cell 34: 7–9.

Green et al.,"Mutational Analysis of HIV–1 Tat Minimal Domain Peptides: Identificaiton of Trans–Dominant Mutants That Suppress HIV–LTR–Driven Gene Expression", Cell 58:215–223.

Groger et al., "Directional antisense and sense cDNA cloning using Epstein–Barr virus episomal expression vectors", Gene 81: 285–294 (1989).

Gudkov et al., "Isolation of genetic suppressor elements, inducing resistance to topoisomerase II–interactive cytotoxic drugs, from human topoisomerase II cDNA", 1993, Proc. Natl. Acad. Sci. USA 90: 3231–3235.

Gussow et al., "The Human $B_2$–Microglobin Gene", J. Immunol. 139: 3132–3138 (1987).

Herskowitz, "Functional Inactivation of Genes by Dominant Negative Mutations", Nature, 329:219–22(1987.

Holzmayer et al. "Isolation of dominant negative mutants and inhibitory antisense RNA sequences by expression selection of random DNA fragments", Nucleic Acids Res 20: 711–717 (1992).

Hunter, "Cooperation between Oncogenes", 1991, Cell 64: 249–270.

Keown et al., "Methods for Introducing DNA into Mammalian Cells", Methods Enzymol 185: 527–536 (1990).

Kern et al., "Mutant p53 proteins bind DNA abnormally in vitro", 1991, Oncogene 6: 131–136.

Kern et al., "Identification of p53 as a Sequence–Specific DNA–Binding Protein", 1991, Science 252: 1708–1711.

Kerr et al., "Excess antisense RNA from infectious recombinant SV–40 fails to inhibit expression of a transfected, interferon–inducible gene", Eur. J. Biochem 175:65–73 (1998).

Kidd V.J. "Dominant Negative Mutation in Galactosyltransferase Created by Over–Expression of a Truncated cDNA", et al., Chemical Abstracts 111(23).

Kim et al., "cDNA Cloning of MEV, a mutant Protein that Facilitates Cellular Uptake of Mevalonate, and Identification of the Point Mutation Responsible for Its Gain of Function", J. Biol. Chem 267: 23113–23121.

Kinzler et al., "Identification of a Gene Located at Chromosome 5q21 that is Mutated in Colorectal Cancers", 1987, Science 236: 70–73.

Kozak and Kabat, "Ping–Pong Amplification of a Retroviral Vector Achieves High–Level Gene Expression: Human Growth Hormone Production", J. Virol 64 3500–3508 (1990).

Kosik et al., "The Primary Structure and Analysis of the Squid Kinesin Heavy Chain", J. Biol. Chem. 265: 3278–3283 (1990).

Kung et al., "Cytotoxic Effects of Cell Cycle Phase Specific Agents: Result of Cell Cycle Perturbation", 1990, Cancer Res. 50:7307–7317.

Laforgia et al., "Receptor protein–tyrosine phosphatase γ is a candidate tumor suppressor gene at human chromosome region 3p21", 1991, Proc. Natl. Acad. Sci. USA 88: 5036–5040.

Lau and Nathans, "Expression of a set of growth–related immediate early genes in BALB/c 3T3 cells: Coordinate regulation with c–fos or c–myc", EMBO J. 4:3145–3151 (1985).

Lee et al., "The retinoblastoma susceptibility gene encodes a nuclear phosphoprotein associated with DNA binding activity", 1987, Nature 329: 642–645.

Lee et al., "Expression of Cloned rpoB Gene of *Escherichia coli*: a Genetic System for the Isolation of Dominant Negative Mutations and Overproduction of Defective B Subunit of RNA Polymerase", J. Bacterial 171:3002–3007 (1989).

Liu et al., "Rational approaches to the Design of Antiviral agents based on S–adenosyl–L–homocysteine hydrolase as a molecular target", 1992, Antivir. Res. 19: 247–265.

Lock et al., "Differential Patterns of Anti–Tumour Drug Responses and Mechanisms of Resistance in a Series of Independently–Derived VP–16–Resistant Human Tumour Cell Lines", J. Cancer 42(3): 371–381 (1988).

Markowitz et al., "Construction and Use of a Safe and Efficient Amphotropic Packaging Cell Line", Virology 167: 400–406 (1988).

McConkey et al., "Glucocorticoids Activate a Suicide Process in Thymosytes through an Elevation of Cytosolic $Ca^{2+}$ Concentration", 1989, Arch. Biochem. Biophys. 269:365–370.

Miller & Rosman, "Improved Retroviral Vectors for Gene Transfer and Expression", Biotechniques 7:980–986 (1989).

Milner et al., "Tumor Suppressor p53: Analysis of Wild-Type and Mutant p53 Complexes", 1991, Molec. Cell. Biol. 11: 12–19.

Montenarh & Quasier, "Two different protein–protein interactions in oligomeric complexes of SV40 large T antigen with cellular oncoproteinp 53", 1989, Oncogene 4: 379–382.

Murphy & Schmike "Pxzd39: a new type of cDNA expression vector for low background, high efficiency directional cloning", Nucleic Acids Res. 19: 3403–3408 (1991).

Murphy and Efstatiadis, "Cloning vectors for expression of cDNA libraries in mammalian cells", Proc. Natl. Acad. Sci. USA 84:8277–8281.

Nakatani et al., "Isolation of an Amplified DNA Sequence in Stomach Cancer", Jpn. J. Cancer Res. 81: 707–710.

Napoli C., "Introduction of a Chimeric Chalcone Synthese Gene into Petunia Results in Reversible Co–Suppression of Homologous Genes in trans", The Plant Cell 2(4):279–289(1990).

Navone et al. "Cloning and Expression of a Human Kinesin Heavy Chain Gene: Interaction of the COOH–terminal Domain with Cytoplasmic Microtubules in Transfected CV–1 Cells", J Cell Biol 117: 1263–1275 (1992).

Noonan et al. "Quantitative analysis of MDRI gene expression in Human tumors by polymerase chain reaction", Proc Natl Acad Sci USA 87:7160–7164 (1990).

O'Rourke et al., "A Potential Transcriptional Activation Element in the p53 protein", 1990, Oncogene 5:1829–1832.

Ohara et al., "One–sided polymerase chain reaction: The Amplification of cDNA", Proc. Natl. Acad. Sci. USA 86:5673–5677 (1989).

Parada et al., "Cooperation between gene encoding p53 tumour antigen and ras in cellular transformation", 1984, Nature 312: 649–651.

Patanjali et al., "Construction of a uniform–abundance (normalized) cDNA library", Proc. Natl. Acad. Sci. USA 88:1943–1947 (1991).

Patterson et al., "Suicide Selection of Mammalian Cell Mutants", Methods Enzymol 151:121(1982).

Pauwels et al., "Rapid and automated terazolium–based colorimetric assay for the detection of anti–HIV Compounds", 1988, J. Virol. Meth. 20: 309–321.

Perlaky et al., "Increased Gr owth of NIH/3T3 Cell by Transfection with Human p120 Complementary DNA and Inhibition by a p120 Antisense Construct", 1992) Cancer Res. 52: 428–436.

Powell et al., "Protection against tobacco mosaic virus in transgenic plants that express tobacco mosaic virus antisense RNA", Proc. Natl. Acad. Sci, USA 86: 6949–6952 (1989).

Ransone et al., "Trans–dominant negative mutants of Fos and Jun", Proc. Natl. Acad. Sci. USA 87:3806–3810 (1990).

Raycroft et al., "Transcriptional Activation by Wild–Type But Not Transforming Mutants of the p53 Anti–Oncogene", 1990, Science 249: 1049–1051.

Rimsky et al., "Trans–dominant inactivation of HTLV–I and HIV–1 gene expression by mutation of the HTLV–I Rex transactivator", Nature 341: 453–456 (1989).

Rio et al., "A Mammalian Host–Vector System That Regulates Expression and Amplification of Transfected Genes by Temperature Induction", Science 227:23–28 (1985).

Sap et al., "The c–erb–A protein is a high–affinity receptor for thyroid hormone", 1986, Nature 324: 635–640.

Sap et al., "Repression of Transcription mediated at a thyroid hormone response element by the v–erb–A oncogene product", 1989, Nature, 340:242–244.

Sarver et al., "Ribozymes as Potential Anti–HIV —1 Therapeutic Agents", Science 247:1222–1225 (1990).

Schneider & Banner, "Building Blocks for Oligonucleotide Analogs with Dimethylene–Sulfide,—Sulfoxide, and —Sulfone Groups Replacing Phosphodiester Linkages", Tethrahedron Letters 31:335 (1990).

Schwab et al., "Amplified DNA in cells of genetic melanoma of Xiphosphorus", 1989, 1989, Oncogene 4:139–144.

Sczakiel G. et al., "Specific inhibition of human Immunodeficiency virus type 1 replication by RNA Transcribed in sense and antisense orientation formteh 5'leader/gag region", Bioch. Biophys. Res. Comm. 169(2):643–651 (1990).

Shen et al., "Human Multidrug–Reistant Cell Lines: Increased mdr1 Expression Can Precede Gene Amplification", Science 232: 643–645 (1986).

Shih et al., "Passage of phenotypes of chemically transformed cells via transfection of DNA and chromatin", 1979, Proc. Natl. Acad Sci. USA 76:5714–5718.

Solomon et al., "Chromosome Aberrations and Cancer", 1991, Science, 254: 1153–1160.

Trent et al., "Identification of a Recurring Translocation Site Involving Chromosome 6 in Human Malignant Melanoma", 1989, Cancer Res. 49: 420–423.

Trono et al., "HIV–1 Gag Mutants Can Dominantly Interfere with the Replication of the Wild–Type Virus", Cell 59:113–120 (1989).

Tsai–Pflugfleder et al. "Cloning and sequencing of cDNA encoding human DNA encoding human DNA topoisomerase II and localization of the gene to chromosome region 17q21–22", Proc. Natl. Acad. Sci USA 85:7177–7181 (1988).

Uhlmann and Peyman "Antisense Oligonucleotides: A New Therapeutic Principle", Chemical Reviews 90: 543–584 (1990).

Vale, "Intracellular Transport Using Microtubule–Based Motors", 1987, Ann. Rev. Cell Biol. 3:347–378.

van der Krol et al., "Modulation of Eukaryotic Gene Expression by Complementary RNA and DNA Sequences", Biotechniques 6:958–976 (1988).

Viskochil et al., "Deletions and a Translocation Interrupt a Cloned Gene at the Neurofibromatosis Type 1 Locus", 1990, Cell 62: 187–192.

Vogelstein et al., "Genetic Alterations During Clorectal–Tumor Development", 1988, N. Engl. J. Med. 319:525–532.

Weinberg "Tumor Suppressor Genes", 1991, Science 254:1138–1146.

Whitaker–Dowling et al., "Cold–Adapted Vaccine Strains of Influenza A Virus Act as Dominant Negative Mutants in Mixed Infections with Wild–Type Influenza A Virus", Virology 175:358–364 (1990).

Wolos et al., "Selective Inhibition of T Cell Activation by an Inhibitor of S–Adenosyl–L–Homocysteine Hydrolase", 1993, J. Immunol, 150:3264–3273.

Xu et al., "The Neurofibromatosis Type 1 Gene Encodes a Protein Related to GAP", 1990, Cell 62: 599–608.

* cited by examiner

FIG. 1A

```
GTGTCTGGGC GGAGCAAAAT ATGTTCCAAT TGTGTTTTCT TTTGATAGAT TCTTTCAACA  60

GACAGTCTTT TCTTAGCATC TTCATTTTTC TTTATTTTGT TGACTTGCAT ATTTTCATTT 120

ACAGGCTGCA ATGGTGACAC TTCCATGGTG ACGGTCGTGA AGGG              164
```

FIG. 1B

```
TGAAAAGATG TATGTCCCAG CTCTCATATT TGGACAGCTC CTAACTTCTA GTAACTATGA   60
TGATGATGAA AAGAAAGTGA CAGGTGGTCG AAATGGCTAT GGAGCCAAAT TGTGTAACAT  120
ATTCAGTACC AAATTTACTG TGGAAACAGC CAGTAGAGAA TACAAGAAAA TGTTCAAACA  180
GACATGGGAT GATAATATGG GAAGAGCTGG TGA                               213
```

FIG. 1C

```
GCCCATTGGT CAGTTTGGTA CCAGGCTACA TGGTGGCAAG GATTCTGCTA GTCCACGATA    60
CATCTTTACA ATGCTCAGCT CTTTGGCTCG ATTGTTATTT CCACCAAAAG ATGATCACAC   120
GTTGAAGTTT TTATATGATG ACAACCAGCG TGTTGAGCCT GAATGGTACA TTCCTATTAT   180
T                                                                  181
```

FIG. 1D

```
TGAATGGTAC ATTCCTATTA TTCCCATGGT GCTGATAAAT GGTGCTGAAG GAATCGGTAC    60
TGGGTGGTCC TGCAAAATCC CCAACTTTGA TGTGCGTGAA ATTGTAAATA ACATCAGGCG   120
TTTGATGGAT GGAGAAGAAC CTTTGCCAAT GCTTCCAAGT TACAAGAACT TCAAGGGTAC   180
TATTGAAGAA CTGGCTCCAA ATCAATATGT GATTAGTGGT GAAG                     224
```

FIG. 1E

```
TGCGTGAAAT TGTAAATAAC ATCAGGCGTT TGATGGATGG AGAAGAACCT TTGCCAATGC    60
TTCCAAGTTA CAAGAACTTC AAGGGTACTA TTGAAGAACT GGCTCCAAAT CAATATGTGA   120
TTAGTGGTGA AGTAGCTATT CTTAATTCTA CAACCATTGA AATCTCAGAG CTTCCCGTCA   180
GAACATGGAC CCAGACATAC AAAGAACAAG TTCTAGAACC CATGTTGAAT GGCACCGAGA   240
AGACACCTCC TCTCATAACA GACTATAGGG AATACCATAC AGATACCACT GTGAAATTTG   300
TTGTGAAGAT GACTGAAGAA AAACTGGCA                                     329
```

FIG. 1F

```
CACTCTTTTC AGTTTCCTTT TCGTTGTCAC TCTCTTCATT TTCTTCTTCA TCTGGAACCT    60
TTTGCTGGGC TTCTTTCCAG GCCTTCACAG GATCCGAATC ATATCCCCTC TGAATCAGAA   120
CTTTAATTAA TTCTTTCTTA GGCTTATTTT CAATGATTAT TTTGCCATCT ATTTCTCTA    180
AGATAAAGCG AGCC                                                    194
```

FIG. 1G

```
TCTGCCTCTG CTTTCATTTC TATGGTTATT CGTGGAATGA CTCTTTGACC ACGCGGAGAA    60
GGCAAAACTT CAGCCATTTG TGTTTTTTC CCCTTGGCCT TCCCCCCTTT CCCAGGAAGT   120
CCGACTTGTT CATCTTGTTT TTCCTTGGCT TCAACAGCCT CCAATTCTTC AATAAATGTA   180
GCCAAGTCTT CTTTCCACAA ATCTGA                                        206
```

FIG. 1H

```
GACACGACAC TTTTCTGTGG TTTCAGTTCT TTGTTACTAA GTTTTGGGGA AGTTTTGGTC    60
TTAGGTGGAC TAGCATCTGA TGGGACAAAA TCTTCATCAT CAGTTTTTTC ATCAAAATCT   120
GAGAAATCTT CATCTGAATC CAAATCCATT GTGAATTTTG TTTTTGTTGC TGCTCTCCGT   180
GGCTCTGTTT CTCG                                                    194
```

FIG. 11

```
CTGAAACCAC AGAAAAGTGT CGTGTCAGAC CTTGAAGCTG ATGATGTTAA GGGCAGTGTA    60
CCACTGTCTT CAAGCCCTCC TGCTACACAT TTCCCAGATG AAACTGAAAT TACAAACCCA   120
GTTCCTAAAA AGAATGTGAC AGTGAAGAAG ACAGCAGCAA AAAGTCAGTC TTCCACCTCC   180
ACTACCGGTG CCAAAAAAAG GGCTGCCCCA AAAGGAACTA AAAGGGATCC AGCTTTGAAT   240
TC                                                                 242
```

FIG. 1J

```
AATTCAAAAGC TGGATCCCTT TTAGTTCCTT TTGGGGCAGC CCTTTTTTG GCACCGGTAG    60
TGGAGGTGGA AGACTGACTT TTTGCTGCTG TCTTCTTCAC TGTCACATTC TTTTTAGGAA   120
CTGGGTTTGT AATTTCAGTT TCATCTGGGA AATGTGTAGC AGGAGGGCTT GAAGACAGTG   180
GTACACTGCC CTTAACATCA TCAGCTTCAA GGTCTGACAC                         220
```

Figure 1K

```
AATTCAAAGC TGGATCCCTT TTAGTTCCTT TTGGGGCAGC CCTTTTTTG GCACCGGTAG    60
TGGAGGTGGA AGACTGACTT TTTGCTGCTG TCTTCTTCAC TGTCACATTC TTTTTAGGAA   120
CTGGGTTTGT AATTTCAGTT TCATCTGGGA AATGTGTAGC AGGAGGGCTT GAAGACAGTG   180
GTACACTGCC CTTAACATCA TCAGCTTCAA GGTCTGACAC                         220
```

Figure 1L

```
GTGTTGAGCC TGAATGGTAC ATTCCTATTA TTCCCATGGT GCTGATAAAT GGTGCTGAAG   60
GAATCGGTAC TGGGTGGTCC TGCAAAATCC CCAACTTTGA TGTGCCTTGAA TTGTAAATA  120
ACATCAGGCG TTTGATGGAT GGAGAAGAAC CTTTGCCCAAT GCTTCCAAGT            170
```

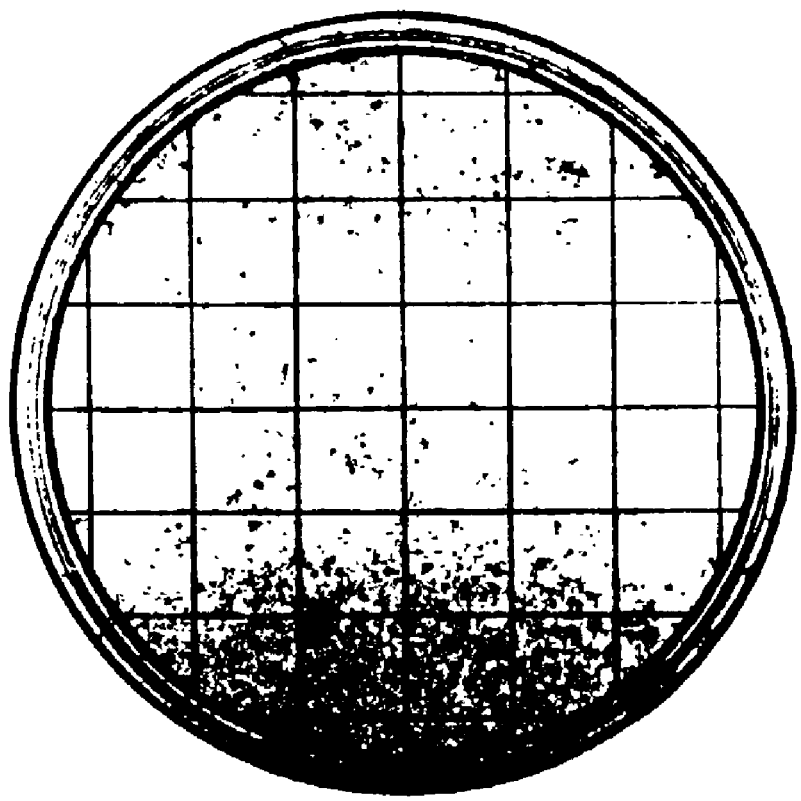
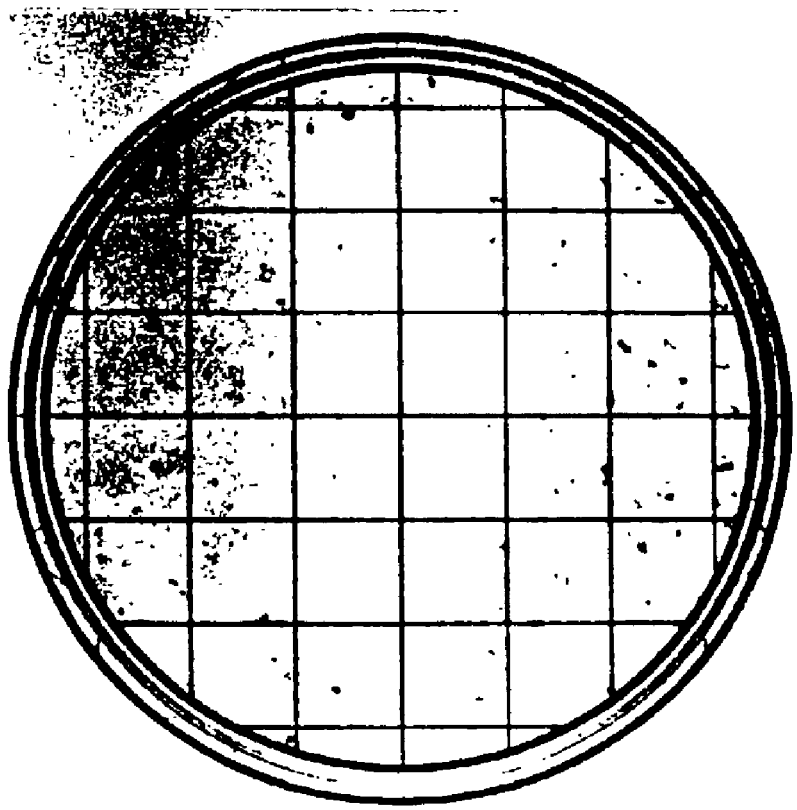
Fig. 5A
infection
control insert-free vector

VPA insert-free vector  VP9-11

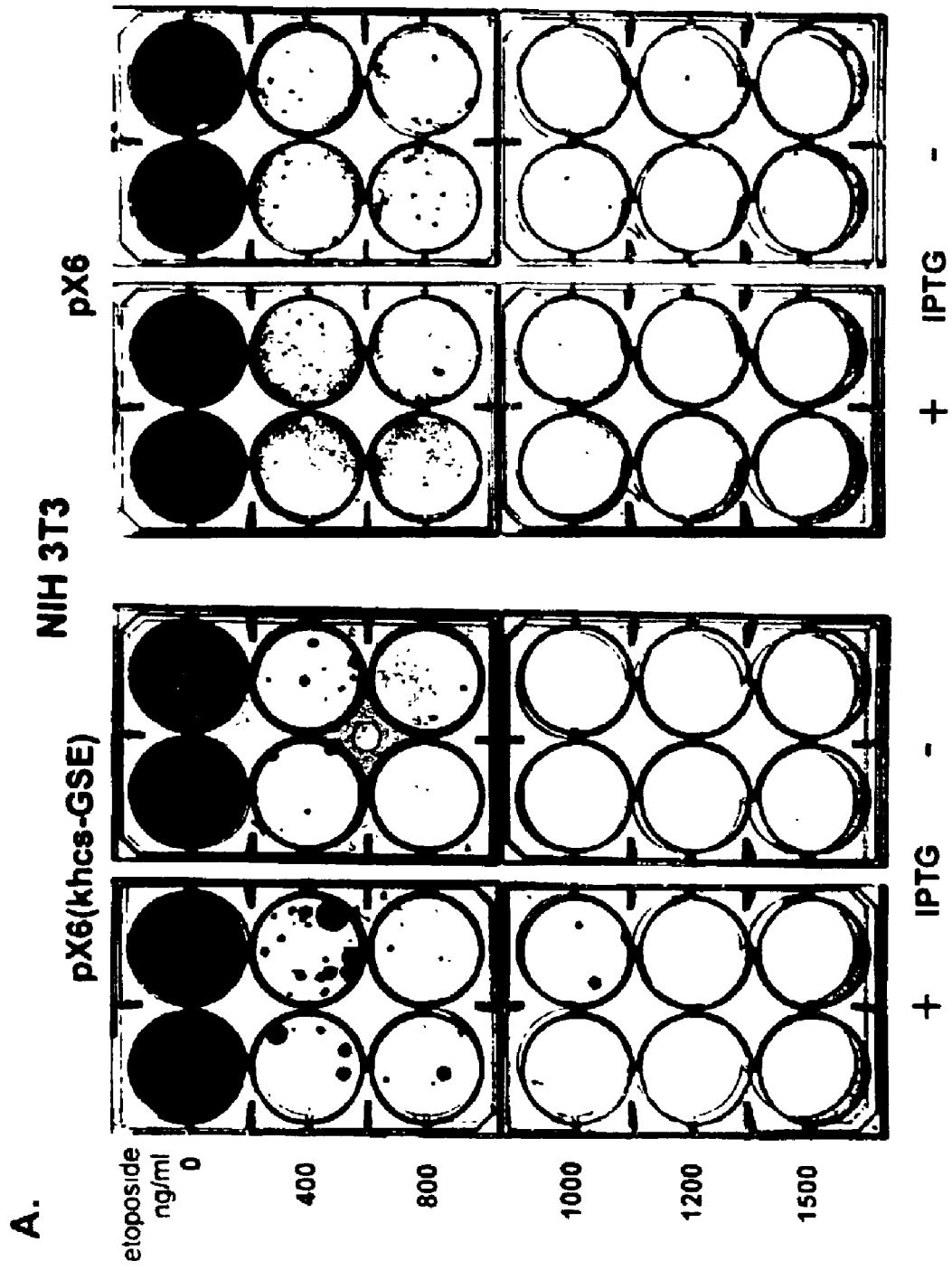

FIG. 9

```
CTTGATCCCT TCTGGTTGAT GCCAGAAGCT CTTCCCTGATC CAGCATTTGT ATCTTCAATT   60
TCTCTACCAA TTGGCTTTGT TGGTTAAATCT CTTCATCCTT GTCATCAAGT TGTTTATACA  120
ATTAGCAAG TTCTTCTTCA CACTTTCTTC TTTCAGCATC GGTAAAACTA CCAGCCATTC  180
CGACTGCAGC AGCTGGTTTA TCACTGGTAA TAGCAATATC TTTATCCGCT GTGAAGGCTT  240
CCAAATTAGC TTTCTCTTTG TCAAACTGCT CATCAATAGG CACTGTCTCC CCGTTACGCC  300
AACGGTTTAG CTCGTTTTCC AGCCACT                                      327
```

FIG. 10

```
CCGACCGGGA GCGGGAGAAG GAGCGGGAGC GGAGAAGGAG CGGGAGAAGG    60
AGCTGGAGCG CGACGGGAGA AGGAACGGGA GCGCGAGCTG GGGAGCAGCG   120
GGCGAGGGAG AAGGAGCTGC TGGCTGCCAA GGCCTTAGAG CCCACCACCT TCCTGCCTGT   180
GGCCGAGCTG CACGGACTCC GAGGTCACAG CACGGAGGAG CCTCGGAGCA   240
GCTGACCCCA   250
```

FIG. 11

```
CTCAGAGGTG ATCCCTCGG AGTCGAGCTC AGGAGAAGGA GTCCCCTTCT TTGAGACTTG    60
GATGCAGACC TGCATGTCCG AGGAGGGCAA GATTTTGAAC CCTGACCATC CCTGCTTCCG   120
CCCTGACTCC ACCGAAGTCG AGTCCTTGGT GGCCCTGCTC AACAACTCTT CAGAGATGAA   180
GCTAGTACAG ATGAAGTAGC ACGAGGCC                                     208
```

FIG. 12A

```
CGACAAACAT CATCTGGGAA GACCCACACG ATGGAGGGTA AACTTCATGA TCCAGAAGGC    60
ATGGAATTA  TTCCAAGAAT AGTGCAAGAT ATTTTTAATT ATATTACTC  CATGGATGAA   120
AATTGGAAT  TTCATATTAA GGTTTCATAT TTTGAAATAT ATTTGGATAA GATAAGGGAC   180
TTGTTAGATG TTTCAAAGAC TAACCTTTCA GTCCATGAAG ACAAAAACCG TGTTCCCTAT   240
GTAAAGGGGT GCACAGAACG TTTCGTGTGT AGTCCAGATG AAGTCATGA  TACCATAGAT   300
GAAGGGAAAT CCAACAGAGA TGTAAAAACAA GAGAATACAC AAACGGAACA GAAACTCAGT   360
CACAGCATAT TTCTTATTAA TGTAAAAACAA GAGAATACAC AAACGGAACA GAAACTCAGT   360
CACAGCATAT TTCTTATTAA TTTAGCTGGC AGTGAGAAGG TTAGTAAGAC TGGGGCTGAA   420
GGAAAGCTTT ATCTGGTTGA TTTAGCTGGC AGTGAGAAGG TTAGTAAGAC TGGGGCTGAA   480
GGTGCTGTGC TGGATGAAGC TAAGAACATC AAGAAGTCAC TTTCTGCACT TGGAAATGTC   540
ATTTCTGCTT TGGCAGAGGG CAGTACCTAT GTTCCTTATC GAGATAGTAA AATGACCAGA   600
ATTCTTCAAG ATTCATTAGG TGGCAACTGT AGGACCACTA TTGTCATATG CTGCTCTCCA   660
TCATCATACA ATGAGTCTGA GACAAAGTCA ACACTCCTCT TGGTCAAAG  GGCCAAAACA   720
ATTAAGAACA CAGTCTGTGT CAATGTAGAG TTAACTGCAG AGCAGTGGAA AAAGAAGTAT   780
```

FIG. 12B

```
GAAAAAGAAA AGGAAAAAAA TAAGACTCTA CGGAACACTA TTCAGTGGCT GGAAAACGAG    840
CTAAACCGTT GGCGTAACGG GGAGACAGTG CCTATTGATG AGCAGTTTGA CAAAGAGAAA    900
GCTAATTTGG AAGCCTTCAC AGCGGATAAA GATACTGCTA TTACCAGTGA TAAACCAGCT    960
GCTGCAGTCG GAATGGCTGG TAGTTTTACC GATGCTGAAA GAAGAAAGTG TGAAGAAGAA   1020
CTTGCTAAAT TGTATAAACA GCTTGATGAC AAGGATGAAG AGATTAACCA ACAAAGCCAA   1080
TTGGTAGAGA AATTGAAGAC ACAAATGCTG GATCAGGAAG AGCTTCTGGC ATCAACCAGA   1140
AGGGATCAAG ATAATATGCA AGCTGAACTG AATGCCTCC AAGCAGAAAA TGATGCTTCT   1200
AAAGAAGAAG TCAAAGAAGT TTTACAGGCC TTAGAGGAAC TGGCTGTTAA TTATGATCAG   1260
AAGTCTCAGG AAGTTGAAGA CAAAACAAAG GAATATGAAT TGCTTAGTGA TGAATTGAAT   1320
CAAAAATCTG CAACTTTAGC AAGTATTGAT GCTGAGCTTC AGAAGCTGAA GGAAATGACC   1380
AACCACCAGA AGAAACGAGC AGCTGAAATG ATGGCATCAT TATTAAAAGA CCTTGCAGAA   1440
ATAGGAATTG CTGTGGGGAA TAACGATGTG AAGCAACCAG AAGGAACTGG TATGATAGAT   1500
GAAGAGTTTA CTGTTGCAAG ACTCTACATT AGCAAAATGA AATCAGAAGT AAAGACCATG   1560
```

FIG. 12C

```
GTGAAACGCT GCAAACAGCT AGAAAGCACG CAGACTGAGA GCAACAAAAA AATGGAAGAA  1620
AATGAGAAAG AGTTAGCAGC ATGCCAGCTT CGGATCTCCC AACATGAAGC CAAAATCAAG  1680
TCACTGACTG AGTACCTTCA GAATGTAGAA CAAAGAAGA GGCAGCTGGA GGAATCTGTT  1740
GATTCCCTTG GTGAGGAGCT AGTCCAACTC CGAGCACAAG AGAAAGTCCA TGAAATGGAA  1800
AAAGAGCACT TGAACAAGGT TCAGACTGCA AATGAAGTCA AGCAAGCTGT TGAGCAGCAG  1860
ATCCAGAGTC ACAGAGAAAC CCACCAAAAA CAAATCAGTA GCTTGCGAGA TGAAGTTGAG  1920
GCAAAGGAAA AGCTAATCAC TGACCTCCAA GACCAAAAAC AGAAGATGGT GTTGGAGCAG  1980
GAACGGCTAA GGGTGGAGCA TGAGAGGCTG AAGGCTACAG ACCAAGAGAA GAGCAGGAAG  2040
CTGCATGAGC TCACGGTTAT GCAAGACAGA CGAGAACAAG CAAGACAAGA CTTGAAGGGT  2100
TTGGAGGAGA CCGTGGCAAA AGAACTTCAG ACTTTACACA ACCTGCGTAA GCTCTTTGTT  2160
CAGGACTTGG CTACCAGGGT GAAAAAGAGG CCGAGGTCGA CTCTGACGAC ACTGGCGGCA  2200
GTGCTGCACA GAAGCAGAAA ATCTCCTTCC TTGAAAACAA CCTTGAACAG CTCACCAAAG  2280
TGCACAAGCA GTTGGTACGT GATAATGCAG ATCTTCGCTG TGAGCTTCCT AAGTTAGAGA  2340
AACGGCTTAG AGCTACTGCA GAAAGAGTGA AAGCTTTGGA GTCAGCCCG              2389
```

Act D
[µg/mL]

Camptothecin
[μg/mL]

Colchicine [μg/mL]

Adriamycin
[μg/mL]

Etoposide
[µg/mL]

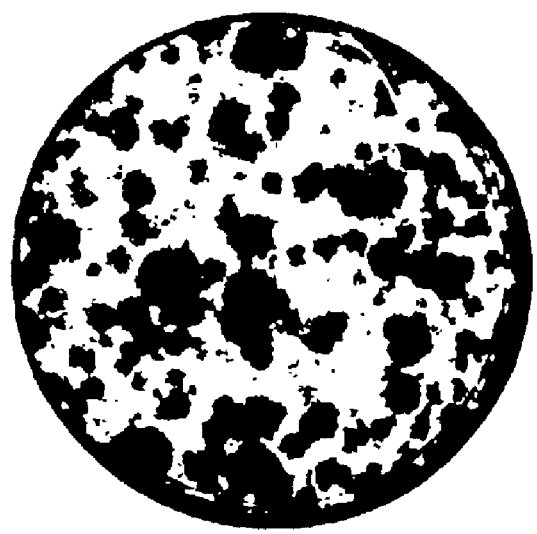
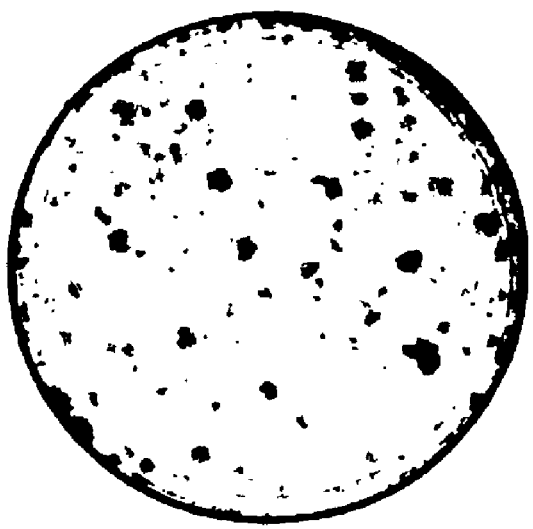
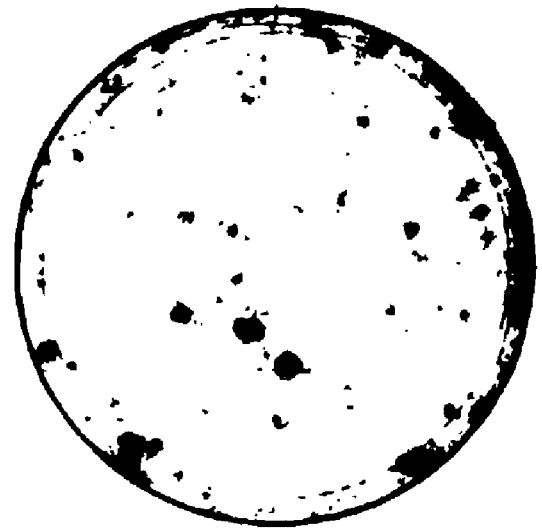
Fig 15

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
        (A) LENGTH: 164 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 1:

```
GTGTCTGGGC GGAGCAAAAT ATGTTCCAAT TGTGTTTTCT TTTGATAGAT TCTTTCAACA        60

GACAGTCTTT TCTTAGCATC TTCATTTTTC TTTATTTTGT TGACTTGCAT ATTTTCATTT       120

ACAGGCTGCA ATGGTGACAC TTCCATGGTG ACGGTCGTGA AGGG                       164
```

(2) INFORMATION FOR SEQ ID NO: 2:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 2:

```
TGAAAAGATG TATGTCCCAG CTCTCATATT TGGACAGCTC CTAACTTCTA GTAACTATGA        60

TGATGATGAA AAGAAAGTGA CAGGTGGTCG AAATGGCTAT GGAGCCAAAT TGTGTAACAT       120

ATTCAGTACC AAATTTACTG TGGAAACAGC CAGTAGAGAA TACAAGAAAA TGTTCAAACA       180

GACATGGATG GATAATATGG GAAGAGCTGG TGA                                    213
```

(2) INFORMATION FOR SEQ ID NO: 3:

(i) SEQUENCE CHARACTERISTICS:
        (A) LENGTH: 181 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 3:

| | | |
|---|---|---|
| GCCCATTGGT CAGTTTGGTA CCAGGCTACA TGGTGGCAAG GATTCTGCTA GTCCACGATA | 60 |
| CATCTTTACA ATGCTCAGCT CTTTGGCTCG ATTGTTATTT CCACCAAAAC ATGATCACAC | 120 |
| GTTGAAGTTT TTATATGATG ACAACCAGCG TGTTGAGCCT GAATGGTACA TTCCTATTAT | 180 |
| T | 181 |

(2) INFORMATION FOR SEQ ID NO: 4:

(i) SEQUENCE CHARACTERISTICS:
    (A) LENGTH: 224 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 4:

| | |
|---|---|
| TGAATGGTAC ATTCCTATTA TTCCCATGGT GCTGATAAAT GGTGCTGAAG GAATCGGTAC | 60 |
| TGGGTGGTCC TGCAAAATCC CCAACTTTGA TGTGCGTGAA ATTGTAAATA ACATCAGGCG | 120 |
| TTTGATGGAT GGAGAAGAAC CTTTGCCAAT GCTTCCAAGT TACAAGAACT TCAAGGGTAC | 180 |
| TATTGAAGAA CTGGCTCCAA ATCAATATGT GATTAGTGGT GAAG | 224 |

(2) INFORMATION FOR SEQ ID NO: 5:

(i) SEQUENCE CHARACTERISTICS:
    (A) LENGTH: 329 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 5:

| | |
|---|---|
| TGCGTGAAAT TGTAAATAAC ATCAGGCGTT TGATGGATGG AGAAGAACCT TTGCCAATGC | 60 |
| TTCCAAGTTA CAAGAACTTC AAGGGTACTA TTGAAGAACT GGCTCCAAAT CAATATGTGA | 120 |
| TTAGTGGTGA AGTAGCTATT CTTAATTCTA CAACCATTGA AATCTCAGAG CTTCCCGTCA | 180 |
| GAACATGGAC CCAGACATAC AAAGAACAAG TTCTAGAACC CATGTTGAAT GGCACCGAGA | 240 |
| AGACACCTCC TCTCATAACA GACTATAGGG AATACCATAC AGATACCACT GTGAAATTTG | 300 |
| TTGTGAAGAT GACTGAAGAA AAACTGGCA | 329 |

(2) INFORMATION FOR SEQ ID NO: 6:

(i) SEQUENCE CHARACTERISTICS:
    (A) LENGTH: 194 base pairs
    (B) TYPE: nucleic acid
    (C) STRANDEDNESS: single (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 6:

CACTCTTTTC AGTTTCCTTT TCGTTGTCAC TCTCTTCATT TTCTTCTTCA TCTGGAACCT      60

TTTGCTGGGC TTCTTTCCAG GCCTTCACAG GATCCGAATC ATATCCCCTC TGAATCAGAA     120

CTTTAATTAA TTCTTTCTTA GGCTTATTTT CAATGATTAT TTTGCCATCT ATTTTCTCAT     180

AGATAAAGCG AGCC                                                      194

(2) INFORMATION FOR SEQ ID NO: 7:

(i) SEQUENCE CHARACTERISTICS:
            (A) LENGTH: 206 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 7:

TCTGCCTCTG CTTTCATTTC TATGGTTATT CGTGGAATGA CTCTTTGACC ACGCGGAGAA      60

GGCAAAACTT CAGCCATTTG TGTTTTTTTC CCCTTGGCCT TCCCCCCTTT CCCAGGAAGT     120

CCGACTTGTT CATCTTGTTT TTCCTTGGCT TCAACAGCCT CCAATTCTTC AATAAATGTA     180

GCCAAGTCTT CTTTCCACAA ATCTGA                                         206

(2) INFORMATION FOR SEQ ID NO: 8:

(i) SEQUENCE CHARACTERISTICS:
            (A) LENGTH: 194 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 8:

GACACGACAC TTTTCTGTGG TTTCAGTTCT TTGTTACTAA GTTTTGGGGA AGTTTTGGTC      60

TTAGGTGGAC TAGCATCTGA TGGGACAAAA TCTTCATCAT CAGTTTTTTC ATCAAAATCT     120

GAGAAATCTT CATCTGAATC CAAATCCATT GTGAATTTTG TTTTTGTTGC TGCTCTCCGT     180

GGCTCTGTTT CTCG                                                      194

(2) INFORMATION FOR SEQ ID NO: 9:

(i) SEQUENCE CHARACTERISTICS:
            (A) LENGTH: 242 base pairs
            (B) TYPE: nucleic acid
            (C) STRANDEDNESS: single
            (D) TOPOLOGY: linear (ii) MOLECULE TYPE: cDNA -continued (iii) HYPOTHETICAL: NO (iv) ANTI-SENSE: YES (xi) SEQUENCE DESCRIPTION: SEQ ID NO: 9:

| | |
|---|---|
| CTGAAACCAC AGAAAAGTGT CGTGTCAGAC CTTGAAGCTG ATGATGTTAA GGGCAGTGTA | 60 |
| CCACTGTCTT CAAGCCCTCC TGCTACACAT TTCCCAGATG AAACTGAAAT TACAAACCCA | 120 |
| GTTCCTAAAA AGAATGTGAC AGTGAAGAAG ACAGCAGCAA AAAGTCAGTC TTCCACCTCC | 180 |
| ACTACCGGTG CCAAAAAAAG GGCTGCCCCA AAAGGAACTA AAGGGATCC AGCTTTGAAT | 240 |
| TC | 242 |

(2) INFORMATION FOR SEQ ID NO: 10:

(i) SEQUENCE CHARACTERISTICS:
        (A) LENGTH: 341 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 10:

| | |
|---|---|
| AACCAGCGTG TTGAGCCTGA ATGGTACATT CCTATTATTC CCATGGTGCT GATAAATGGT | 60 |
| GCTGAAGGAA TCGGTACTGG GTGGTCCTGC AAAATCCCCA ACTTTGATGT GCGTGAAATT | 120 |
| GTAAATAACA TCAGGCGTTT GATGGATGGA AAGAACCTT TGCCAATGCT TCCAAGTTAC | 180 |
| AAGAACTTCA AGGGTACTAT TGAAGAACTG GCTCCAAATC AATATGTGAT TAGTGGTGAA | 240 |
| GTAGCTATTC TTAATTCTAC AACCATTGAA ATCTCAGAGC TTCCCGTCAG AACATGGACC | 300 |
| CAGACATACA AAGAACAAGT TCTAGAACCC ATGTTGAATG G | 341 |

(2) INFORMATION FOR SEQ ID NO: 11:

(i) SEQUENCE CHARACTERISTICS:
        (A) LENGTH: 220 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 11:

| | |
|---|---|
| AATTCAAAGC TGGATCCCTT TTAGTTCCTT TTGGGGCAGC CCTTTTTTTG GCACCGGTAG | 60 |
| TGGAGGTGGA AGACTGACTT TTTGCTGCTG TCTTCTTCAC TGTCACATTC TTTTTAGGAA | 120 |
| CTGGGTTTGT AATTTCAGTT TCATCTGGGA AATGTGTAGC AGGAGGGCTT GAAGACAGTG | 180 |
| GTACACTGCC CTTAACATCA TCAGCTTCAA GGTCTGACAC | 220 |

(2) INFORMATION FOR SEQ ID NO: 12:

(i) SEQUENCE CHARACTERISTICS:
        (A) LENGTH: 170 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 12:

GTGTTGAGCC TGAATGGTAC ATTCCTATTA TTCCCATGGT GCTGATAAAT GGTGCTGAAG      60

GAATCGGTAC TGGGTGGTCC TGCAAAATCC CCAACTTTGA TGTGCGTGAA TTGTAAAATA     120

ACATCAGGCG TTTGATGGAT GGAGAAGAAC CTTTGCCAAT GCTTCCAAGT               170

(2) INFORMATION FOR SEQ ID NO: 13:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 13:

AATCATCGAT GGATGGATGG                                                  20

(2) INFORMATION FOR SEQ ID NO: 14:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 14:

CCATCCATCCATCGATGATTAAA                                                23

(2) INFORMATION FOR SEQ ID NO: 15:

(i) SEQUENCE CHARACTERISTICS:
            (A) LENGTH: 327 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 15:

CTTGATCCCT TCTGGTTGAT GCCAGAAGCT CTTCCTGATC CAGCATTTGT ATCTTCAATT      60

TCTCTACCAA TTGGCTTTGT TGGTTAATCT CTTCATCCTT GTCATCAAGT TGTTTATACA     120

ATTTAGCAAG TTCTTCTTCA CACTTTCTTC TTTCAGCATC GGTAAAACTA CCAGCCATTC     180

CGACTGCAGC AGCTGGTTTA TCACTGGTAA TAGCAATATC TTTATCCGCT GTGAAGGCTT     240

CCAAATTAGC TTTCTCTTTG TCAAACTGCT CATCAATAGG CACTGTCTCC CCGTTACGCC     300

```
AACGGTTTAG CTCGTTTTCC AGCCACT                                                327
```

(2) INFORMATION FOR SEQ ID NO: 16:

(i) SEQUENCE CHARACTERISTICS:
        (A) LENGTH: 250 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 16:

```
CCGACCGGGA GCGGGAGAAG GAGCGGGAGC GGGAGCAGCG GGAGAAGGAG CGGGAGAAGG       60
AGCTGGAGCG CGACGGGAGA AGGAACGGGA GCGCGAGCTG GAGCGGCAGC GGGAGCAGCG      120
GGCGAGGGAG AAGGAGCTGC TGGCTGCCAA GGCCTTAGAG CCCACCACCT TCCTGCCTGT      180
GGCCGAGCTG CACGGACTCC GAGGTCACAG CACGGAGGAG CGGCCCAAGC CCTCGGAGCA      240
GCTGACCCCA                                                             250
```

(2) INFORMATION FOR SEQ ID NO: 17:

(i) SEQUENCE CHARACTERISTICS:
        (A) LENGTH: 208 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 17:

```
CTCAGAGGTG ATCCTCTCGG AGTCGAGCTC AGGAGAAGGA GTCCCCTTCT TTGAGACTTG       60
GATGCAGACC TGCATGTCCG AGGAGGGCAA GATTTTGAAC CCTGACCATC CCTGCTTCCG      120
CCCTGACTCC ACCGAAGTCG AGTCCTTGGT GGCCCTGCTC AACAACTCTT CAGAGATGAA      180
GCTAGTACAG ATGAAGTAGC ACGAGGCC                                         208
```

(2) INFORMATION FOR SEQ ID NO: 18:

(i) SEQUENCE CHARACTERISTICS:
        (A) LENGTH: 2389 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 18:

```
CGACAAACAT CATCTGGGAA GACCCACACG ATGGAGGGTA AACTTCATGA TCCAGAAGGC       60
ATGGGAATTA TTCCAAGAAT AGTGCAAGAT ATTTTTAATT ATATTTACTC CATGGATGAA      120
AATTTGGAAT TCATATTAA GGTTTCATAT TTTGAAATAT ATTTGGATAA GATAAGGGAC       180
TTGTTAGATG TTTCAAAGAC TAACCTTTCA GTCCATGAAG ACAAAAACCG TGTTCCCTAT      240
GTAAAGGGGT GCACAGAACG TTTCGTGTGT AGTCCAGATG AAGTCATGGA TACCATAGAT      300
GAAGGGAAAT CCAACAGAGA TGTCGCAGTT ACAAATATGA ATGAACATAG CTCTAGGAGC      360
```

-continued

```
CACAGCATAT TTCTTATTAA TGTAAAACAA GAGAATACAC AAACGGAACA GAAACTCAGT      420

GGAAAGCTTT ATCTGGTTGA TTTAGCTGGC AGTGAGAAGG TTAGTAAGAC TGGGGCTGAA      480

GGTGCTGTGC TGGATGAAGC TAAGAACATC AAGAAGTCAC TTTCTGCACT TGGAAATGTC      540

ATTTCTGCTT TGGCAGAGGG CAGTACCTAT GTTCCTTATC GAGATAGTAA AATGACCAGA      600

ATTCTTCAAG ATTCATTAGG TGGCAACTGT AGGACCACTA TTGTCATATG CTGCTCTCCA      660

TCATCATACA ATGAGTCTGA GACAAAGTCA ACACTCCTCT TTGGTCAAAG GGCCAAAACA      720

ATTAAGAACA CAGTCTGTGT CAATGTAGAG TTAACTGCAG AGCAGTGGAA AAAGAAGTAT      780

GAAAAGAAA AGGAAAAAAA TAAGACTCTA CGGAACACTA TTCAGTGGCT GGAAAACGAG       840

CTAAACCGTT GGCGTAACGG GGAGACAGTG CCTATTGATG AGCAGTTTGA CAAAGAGGAA      900

GCTAATTTGG AAGCCTTCAC AGCGGATAAA GATACTGCTA TTACCAGTGA TAAACCAGCT      960

GCTGCAGTCG GAATGGCTGG TAGTTTTACC GATGCTGAAA GAAGAAAGTG TGAAGAAGAA     1020

CTTGCTAAAT TGTATAAACA GCTTGATGAC AAGGATGAAG AGATTAACCA ACAAAGCCAA     1080

TTGGTAGAGA AATTGAAGAC ACAAATGCTG GATCAGGAAG AGCTTCTGGC ATCAACCAGA     1140

AGGGATCAAG ATAATATGCA AGCTGAACTG AATCGCCTCC AAGCAGAAAA TGATGCTTCT     1200

AAAGAAGAAG TCAAAGAAGT TTTACAGGCC TTAGAGGAAC TGGCTGTTAA TTATGATCAG     1260

AAGTCTCAGG AAGTTGAAGA CAAAACAAAG GAATATGAAT TGCTTAGTGA TGAATTGAAT     1320

CAAAAATCTG CAACTTTAGC AAGTATTGAT GCTGAGCTTC AGAAGCTGAA GGAAATGACC     1380

AACCACCAGA AGAAACGAGC AGCTGAAATG ATGGCATCAT TATTAAAAGA CCTTGCAGAA     1440

ATAGGAATTG CTGTGGGGAA TAACGATGTG AAGCAACCAG AAGGAACTGG TATGATAGAT     1500

GAAGAGTTTA CTGTTGCAAG ACTCTACATT AGCAAAATGA AATCAGAAGT AAAGACCATG     1560

GTGAAACGCT GCAAACAGCT AGAAAGCACG CAGACTGAGA GCAACAAAAA AATGGAAGAA     1620

AATGAGAAAG AGTTAGCAGC ATGCCAGCTT CGGATCTCCC AACATGAAGC CAAAATCAAG     1680

TCACTGACTG AGTACCTTCA GAATGTAGAA CAAAAGAAGA GGCAGCTGGA GGAATCTGTT     1740

GATTCCCTTG GTGAGGAGCT AGTCCAACTC CGAGCACAAG AGAAAGTCCA TGAAATGGAA     1800

AAAGAGCACT TGAACAAGGT TCAGACTGCA AATGAAGTCA AGCAAGCTGT TGAGCAGCAG     1860

ATCCAGAGTC ACAGAGAAAC CCACCAAAAA CAAATCAGTA GCTTGCGAGA TGAAGTTGAG     1920

GCAAAGGAAA AGCTAATCAC TGACCTCCAA GACCAAAACC AGAAGATGGT GTTGGAGCAG     1980

GAACGGCTAA GGGTGGAGCA TGAGAGGCTG AAGGCTACAG ACCAAGAGAA GAGCAGGAAG     2040

CTGCATGAGC TCACGGTTAT GCAAGACAGA CGAGAACAAG CAAGACAAGA CTTGAAGGGT     2100

TTGGAGGAGA CCGTGGCAAA AGAACTTCAG ACTTTACACA ACCTGCGTAA GCTCTTTGTT     2160

CAGGACTTGG CTACCAGGGT GAAAAAGAGG CCGAGGTCGA CTCTGACGAC ACTGGCGGCA     2220

GTGCTGCACA GAAGCAGAAA ATCTCCTTCC TTGAAAACAA CCTTGAACAG CTCACCAAAG     2280

TGCACAAGCA GTTGGTACGT GATAATGCAG ATCTTCGCTG TGAGCTTCCT AAGTTAGAGA     2340

AACGGCTTAG AGCTACTGCA GAAAGAGTGA AAGCTTTGGA GTCAGCCCG               2389
```

(2) INFORMATION FOR SEQ ID NO: 19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA -continued (iii) HYPOTHETICAL: NO (iv) ANTI-SENSE: YES (xi) SEQUENCE DESCRIPTION: SEQ ID NO: 19:

AGTGGCTGGA AAACGAGCTA                                              20

(2) INFORMATION FOR SEQ ID NO: 20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 20:

CTTGATCCCT TCTGGTTGAT                                              20

(2) INFORMATION FOR SEQ ID NO: 21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 21:

AGTGGCTTGA AAATGAGCTC                                              20

(2) INFORMATION FOR SEQ ID NO: 22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 22:

CTTGATCCCT TCTGGTAGAT G                                            21

GENES AND GENETIC ELEMENTS ASSOCIATED WITH SENSITIVITY TO CHEMOTHERAPEUTIC DRUGS

This is a divisional of U.S. Ser. No. 09/568,315, filed May 9, 2000, now U.S. Pat. No. 6,326,488, issued Dec. 4, 2001, which is a divisional application of U.S. Ser. No. 08/929,208, filed Sep. 9, 1997, now U.S. Pat. No. 6,060,244, issued May 9, 2000, which is a divisional of U.S. Ser. No. 08/480,552, filed Jun. 7, 1995, now U.S. Pat. No. 5,665,550, issued Sep. 9, 1997, which is a continuation of U.S. Ser. No. 08/033,086, filed Mar. 9, 1993, now abandoned, which is a continuation-in-part of international application PCT/US91/07492, filed as international application on Oct. 11, 1991, which is a continuation-in-part of U.S. Ser. No. 07/599,730, filed Oct. 19, 1990 now U.S. Pat. No. 5,217,889, issued Jun. 8, 1993.

This invention was made with government support under grants CA39365 and CA-56738 by the National Institutes of Health. The government has certain rights in the invention.

BACKGROUND OF THE INVENTION

1. Field of the Invention

The invention relates to genetic factors associated with sensitivity to chemotherapeutic drugs. More particularly, the invention relates to methods for identifying such factors as well as to uses for such factors.

2. Summary of the Related Art

A broad variety of chemotherapeutic agents are used in the treatment of human cancer. For example the textbook *CANCER: Principles & Practice Of Oncology*, 2d Edition, (De Vita et al., Eds.), J.B. Lippincott Company, Philadelphia, Pa. (1985) discloses as major antineoplastic agents the plant alkaloids vincristine, vinblastine, vindesine, and VM-26; the antibiotics antinomycin-D, doxorubicin, daunorubicin, mithramycin, mitomycin C and bleomycin; the antimetabolites methotrexate, 5-fluorouracil, 5-fluorodeoxyuridine, 6-mercaptopurine, 6-thioguanine, cytosine arabinoside, 5-aza-cytidine and hydroxyurea; the alkylating agents cyclophosphamide, melphalan, busulfan, CCNU, MeCCNU, BCNU, streptozotocin, chlorambucil, cis-diamminedichloroplatinum, azetidinylbenzoquinone; and the miscellaneous agents dacarbazine, mAMSA and mitoxantrone.

These and other chemotherapeutic agents such as etoposide and amsacrine have proven to be very useful in the treatment of cancer. Unfortunately, some tumor cells become resistant to specific chemotherapeutic agents, in some instances even to multiple chemotherapeutic agents. Such drug resistance or multiple drug resistance can theoretically arise from either the presence of genetic factors that confer resistance to the drugs, or from the absence of genetic factors that confer sensitivity to the drugs. The former type of factors have been identified, and include the multiple drug resistance gene mdr-1 (see Chen et al., Cell 47:381–389 (1986)). However, the latter type of factor remains largely unknown, perhaps in part because such absence of factors would ten to be a recessive trait.

Identification of genes associated with sensitivity to chemotherapeutic agents is desirable, because the discovery of such genes can lead to both diagnostic and therapeutic approaches for cancer cells and for drug resistance cancer cells, as well as to improvements in gene therapy and rational drug design. Recently, some developments have been made in the difficult area of isolating recessive genetic elements, including one involved in cytotoxic drug sensitivity. Roninson et al., U.S. Pat. No. 5,217,889 (Ser. No. 07/599,730 issued Jun. 8, 1993) teaches a generalized method for obtaining genetic suppressor elements (GSEs), which are dominant negative factors that confer the recessive-type phenotype for the gene to which the particular GSE corresponds. (See also Holzmayer et al., Nucleic Acids Res. 20:711–717 (1992). Gudkov et al., Proc. Natl. Acad. Sci. USA 90: 3231–3235 (1993) teaches isolation of GSEs inducing resistance to topoisomerase II-interactive drugs from topoisomerase II cDNA. However, there remains a need for identifying yet unknown genes or genetic elements associated with sensitivity to chemotherapeutic agents, a task made more difficult by the unavailability of a cloned gene as starting material for preparing GSEs. Preferably, such genes or genetic elements will be involved in a common pathway that is implicated in sensitivity to more than one chemotherapeutic agent. Most preferably, such genes or genetic elements will be identified by direct selection of GSEs causing loss of the drug sensitivity phenotype.

BRIEF SUMMARY OF THE INVENTION

The invention provides genetic suppressor elements (GSEs) that confer upon cells resistance to chemotherapeutic drugs. These GSEs are random fragments derived from genes associated with sensitivity to chemotherapeutic drugs, although the nature of such genes can be quite surprising.

In a first aspect, the invention provides a method for identifying GSEs that confer resistance to any chemotherapeutic drug for which resistance is possible. This method utilizes chemotherapeutic drug selection of cells that harbor clones from a random fragment expression library derived from total cDNA and subsequent rescue of library inserts from drug-resistant cells. In a second aspect, the invention provides a method for identifying and cloning genes that are associated with sensitivity to chemotherapeutic drugs, including genes that have not been previously discovered. This method comprises the steps of screening a full length cDNA library with a GSE that confers upon cells resistance to chemotherapeutic (or an oligonucleotide or polynucleotide constituting a portion of such a GSE) and determining the nucleotide sequence of the cDNA insert of any positive clones obtained. In a third aspect, the invention provides a method for obtaining GSEs having optimized suppressor activity for a gene associated with sensitivity to a chemotherapeutic drug. This method utilizes chemotherapeutic drug selection of cells that harbor clones from a random fragment expression library derived from DNA of a gene associated with sensitivity to the same chemotherapeutic drug, and subsequent rescue of the library inserts from drug resistance cells. In a fourth aspect, the invention provides synthetic peptides and oligonucleotides that confer upon cells resistance to chemotherapeutic drugs. These synthetic peptides and oligonucleotides are designed based upon the sequence of a drug-resistance conferring GSEs according to the invention.

In a fifth aspect, the invention provides a diagnostic assay for tumor cells that are resistant to one or more chemotherapeutic drug due to the absence of expression or underexpression of a particular gene. This diagnostic assay comprises quantitating the level of expression of the particular gene product by a particular tumor cell sample to be tested. In a sixth aspect, the invention provides dominated selectable markers that are useful in gene co-transfer studies. These dominant selectable markers are drug resistance-conferring GSEs according to the invention operably linked to appropriate transcriptional control elements. In a seventh aspect, the invention provides in vivo-selectable markers that are useful both for gene therapy and for enhanced chemotherapy for cancer. Such in vivo selectable markers are transferred into blood progenitor cells, which are then used to repopulate the patient's blood exclusively with cells that contain a co-transferred therapeutic gene, or for chemotherapy, just the chemotherapeutic drug resistance conferring GSE. In an eighth aspect, the invention provides a starting point for the rational design of pharmaceutical products that are useful against tumor cells that are resistant to chemotherapeutic drugs. By examining the structure, function, localization and pattern of expression of genes associated with sensitivity to chemotherapeutic drugs, strategies can be developed for creating pharmaceutical products that will overcome drug resistance in tumor cells in which such genes are either not expressed or underexpressed.

BRIEF DESCRIPTION OF THE DRAWINGS

FIGS. 1A through 1L shows the nucleotide sequences of twelve GSEs that confer etoposide resistance upon cells and that were derived from topoisomerase II DNA, using a single gene random fragment expression library, as described in Example 1. The GSEs shown are FIG. 1A clone 2V [SEQ. ID. NO. 1], FIG. 1B clone Σ11 [SEQ. ID. NO. 2], FIG. 1C clone 6 [SEQ. ID. NO. 3, FIG. 1D clone 5 [SEQ. ID. NO. 4], FIG. 1E clone Σ28 [SEQ. ID. NO. 5], FIG. 1F clone Σ2 [SEQ. ID. NO. 6], FIG. 1G clone Σ20 [SEQ. ID. NO. 7], FIG. 1H clone 39 [SEQ. ID. NO. 8], FIG. 1J clone 12S [SEQ. ID. NO. 9], FIG. 1J clone Σ8 [SEQ. ID. NO. 10], FIG. 1K clone ΣVPs2 [SEQ. ID. NO. 11], and FIG. 1L clone ΣVM [SEQ. ID. NO. 12].

FIG. 2A shows the overall construction scheme. FIG. 2B shows normalization of the cDNA fragments. FIG. 2B, t represents total unfractionated cDNA, s and d represent the single-stranded and double-stranded fractions separated by hydroxyapatite, time points indicate the period of reannealing, and tubulin, c-myc, and c-fos indicate the probes used in Southern hybridization with the total, single-stranded and double-stranded fractions.

FIGS. 5A and 5B shows etoposide resistance conferred by preselected virus FIG. 5A and PCR analysis of the selected and unselected populations FIG. 5B.

FIGS. 8A and 8B shows resistance to various concentrations of etoposide, conferred upon the cells by the GSE anti-khcs under an IPTG-inducible promoter FIG. 8A and the scheme for this selection FIG. 8B.

FIG. 9 shows the nucleotide sequence of the GSE anti-khcs [SEQ. ID. NO. 15].

FIG. 10 shows the nucleotide sequence of the GSE VPA [SEQ. ID. NO. 16].

FIG. 11 shows the nucleotide sequence of the GSE VP9-11 [SEQ. ID. NO. 17].

FIGS. 12A through 12C shows the nucleotide sequence of the most of the coding region of the mouse khcs cDNA [SEQ. ID. NO. 18].

FIG. 15 demonstrates increased immortalization of primary mouse embryo fibroblasts by infection with the LNCX vector containing the anti-khcs GSE, relative to cells infected with the LNCX vector alone or uninfected (control) cells.

DETAILED DESCRIPTION OF THE PREFERRED EMBODIMENTS

Figure 2A:
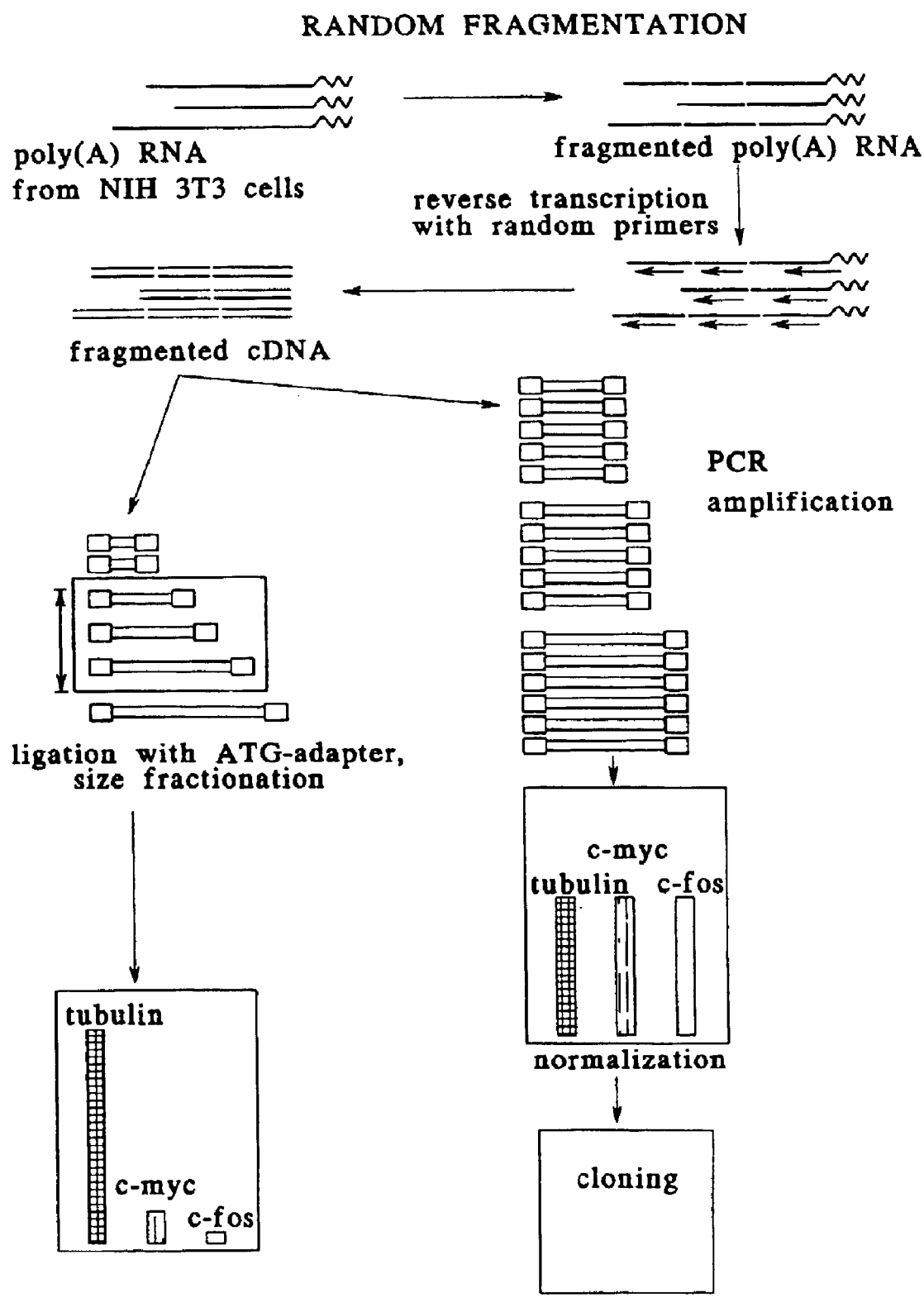
FIGS. 2A and 2B shows a scheme for construction of RFEL from NIH 3T3 cDNA.

The invention relates to means for suppressing specific gene functions that are associated with sensitivity to chemotherapeutic drugs. The invention provides genetic suppressor elements (GSEs) that have such suppressive effect and thus confer resistance to chemotherapeutic drugs. The invention further provides methods for identifying such GSEs, as well as methods for their use.

In a first aspect, the invention provides a method for identifying GSEs that confer resistance to any chemotherapeutic drug for which resistance is possible. The GSEs identified by this method will be homologous to a gene that is associated with sensitivity to one or more chemotherapeutic drug. For purposes of the invention, the term "homologous to a gene" has two different meanings, depending on whether the GSE acts through an antisense or antigene mechanism, or rather through a mechanism of interference at the protein level. In the former case, a GSE that is an antisense or antigen oligonucleotide or polynucleotide is homologous to a gene if it has a nucleotide sequence that hybridizes under physiological conditions to the gene or its mRNA transcript by Hoogsteen or Watson-Crick base-pairing. In the latter case, a GSE that interferes with a protein molecule is homologous to the gene encoding that protein molecule if it has an amino acid sequence that is the same as that encoded by a portion of the gene encoding the protein, or that would be the same, but for conservative amino acid substitutions. In either case, as a practical matter, whether the GSE is homologous to a gene is determined by assessing whether the GSE is capable of inhibiting or reducing the function of the gene.

The method according to this aspect of the invention comprises the step of screening a total cDNA or genomic DNA random fragment expression library phenotypically to identify clones that confer resistance to a chemotherapeutic drug. Preferably, the library of random fragments of total cDNA or genomic DNA is cloned into a retroviral expression vector. In this preferred embodiment, retrovirus particles containing the library are used to infect cells and the infected cells are tested for their ability to survive in a concentration of a chemotherapeutic drug that kills uninfected cells. Preferably, the inertia in the library will range in size from about 100 b.p. to about 700 b.p. and more preferably, from about 200 b.p. to about 500 b.p. Most preferably, the random fragment library will be a normalized library containing roughly equal numbers of clones corresponding to each gene expressed in the cell type from which it was made, without regard for the level of expression of any gene. However, normalization of the library is unnecessary for the isolation of GSEs that are homologous to abundantly or moderately expressed genes. Once a clonal population of cells that are resistant to the chemotherapeutic drug has been isolated, the library clone encoding the GSE is rescued from the cells. At this stage, the insert of the expression library may be tested for its nucleotide sequence. Alternatively, the rescued library clone may be further tested for its ability to confer resistance to chemotherapeutic drugs in additional transfection or infection and selection assays, prior to nucleotide sequence determination. Determination of the nucleotide sequence, of course, results in the identification of the GSE. This method is further illustrated in Examples 2–5.

In a second aspect, the invention provides a method for identifying and cloning genes that are associated with sensitivity to chemotherapeutic drugs, including genes that have not been previously discovered. This is because GSEs, or portions thereof, can be used as probes to screen full length cDNA or genomic libraries to identify their gene of origin. In some cases, genes that are associated with sensitivity to chemotherapeutic drugs will turn out to be quite surprising. For example, GSEs that abrogate etoposide sensitivity are of a particularly surprising nature. The target for etoposide is topoisomerase IL, a DNA unwinding enzyme. GSEs prepared from random fragments of topoisomerase II DNA do confer resistance to etoposide. Accordingly, it would be expected that most GSEs conferring etoposide resistance would be derived from DNA encoding toposisomerase II. Surprisingly, this is not the case at all. Of three etoposide resistance-conferring GSEs obtained, two were derived from previously unidentified DNA sequences. A third such GSE was derived from the kinesin heavy chain gene. Prior to this discovery, there was no suspicion that kinesin was in any way implicated in etoposide sensitivity. These results suggest that the method according to this aspect of the invention will provide much new and surprising information about the genetic basis for resistance to chemotherapeutic drugs. In addition, a kinesin-derived GSE conferring resistance to etoposide caused cellular effects suggesting that kinesin may be involved in programmed cell death. If this is indeed the case, then the method according to this aspect of the invention also provides valuable information about the genetic basis for senescence and cell death. This may have important implications for studying genes involved in development, since GSEs used to identify genes associated with chemotherapeutic drug resistance or senescence can also be expressed as transgenes in embryos to determine the role of such genes in development. The method according to this aspect of the invention and its use for studying genes identified thereby and their cellular effects are further illustrated in Examples 6–8.

In a third aspect, the invention provides a method for obtaining GSEs having optimized suppressor activity for a gene associated with sensitivity to a chemotherapeutic drug. In the method according to this aspect of the invention, an initial GSE is obtained by the method according to the first aspect of the invention. Then, the gene from which the GSE is derived is identified and cloned by the method according to the second aspect of the invention. This gene is then randomly fragmented and cloned into an expression vector, preferably a retroviral vector, to obtain a random fragment expression library derived exclusively from the gene of interest. This library is then transferred to and expressed in mammalian cells, which are selected in the presence of the appropriate chemotherapeutic drug. As a practical matter, such a library will contain a much greater variety of GSEs derived from the gene of interest than will a random fragment library prepared from total cDNA. Consequently, the likelihood of obtaining optimized GSEs, as determined by maximized chemotherapeutic drug resistance, from the single gene random fragment library is much higher. A single gene random fragment library approach is shown in greater detail in Example 1.

In a fourth aspect, the invention provides synthetic peptides and oligonucleotides that are capable of inhibiting the function of genes associated with sensitivity to chemotherapeutic drugs. Synthetic peptides according to the invention have amino acid sequences that correspond to amino acid sequences encoded by GSEs according to the invention. Synthetic oligonucleotides according to the invention have nucleotide sequences corresponding to the nucleotide sequences of GSEs according to the invention. Once a GSE is discovered and sequenced, and its orientation is determined, it is straightforward to prepare an oligonucleotide corresponding to the nucleotide sequence of the GSE (for antisense-oriented GSEs) or amino acid sequence encoded by the GSE (for sense-oriented GSEs). In certain embodiments, such synthetic peptides or oligonucleotides may have the complete sequence encoded by the GSE or may have only part of the sequence present in the GSE, respectively. In certain other embodiments, the peptide or oligonucleotide may have only a portion of the GSE-encoded or GSE sequence. In such latter embodiments, undue experimentation is avoided by the observation that many independent GSE clones corresponding to a particular gene will have the same 5' or 3' terminus, but generally not both. This suggests that many GSEs have one critical endpoint, form which a simple walking experiment will determine the minimum size of peptide or oligonucleotide necessary to inhibit gene function. For peptides, functional domains as small as 6–8 amino acids have been identified for immunoglobulin binding regions. Thus, peptides or peptide mimetics having these or larger dimensions can be prepared as GSEs. For antisense oligonucleotides, inhibit of gene function can be mediated by oligonucleotides having sufficient length to hybridize to their corresponding mRNA under physiological conditions. Generally, oligonucleotides having about 12 or more buses will fit this description. Preferably, such oligonucleotides will have from about 12 to about 100 nucleotides. As used herein, the term oligonucleotide includes modified oligonucleotides having nuclear-resistant internucleotide linkages, such as phosphorothioate, methylphosphonate, phosphorodithioate, phosphoramidate, phosphotriester, sulfone, siloxane, carbonate, carboxymethylester, acetamidate, carbamate, thioether, bridged phosphoramidate, bridged methylene phosphonate and bridged phosphorothioate internucleotide linkages. The synthesis of oligonucleotides containing these modified linkages is well known in the art. (See e.g., Uhlmann and Peyman, Chemical Reviews 90:543–584 (1990); Schneider and Banner, Tetrahedron Letters 31:335 (1990)). The term oligonucleotides also includes oligonucleotides having modified bases or modified ribose or deoxyribose sugars.

In a fifth aspect, the invention provides a diagnostic assay for tumor cells that are resistant to one or more chemotherapeutic drug due to absence of expression or underexpression of a particular gene. By using the methods according to the first and second aspects of the invention such a gene will be identified and cloned. To determine whether absence or expression or underexpression of such a gene is a naturally occurring, and thus medically significant basis for chemotherapeutic drug resistance, human tumor cells can be treated with cytotoxic quantities of an appropriate chemotherapeutic drug to select for spontaneous drug resistant mutants. These mutants can then be assessed for their level of expression of the particular gene of interest. Absence of expression or significantly reduced expression indicates a natural mechanism of chemotherapeutic drug resistance. Accordingly, such reduced or absent expression can be the basis for a diagnostic assay for tumor cell resistance to the chemotherapeutic drug or drugs of interest. A first embodiment of a diagnostic assay according to this aspect of the invention utilizes an oligonucleotide or oligonucleotides that is/are homologous to the sequence of the gene for which expression is to be measured. In this embodiment, RNA is extracted from a tumor sample, and RNA specific for the gene of interest is quantitated by standard filter hybridization procedures, an RNase protection assay, or by quantitative cDNA-PCR. (See Noonan et al., Proc. Natl. Acad. Sci. USA 87:7160–7164 (1990)). In a second embodiment of a diagnostic assay according to this aspect of the invention, antibodies are raised against a synthetic peptide having an amino acid sequence that is identical to a portion of the protein that is encoded by the gene of interest. These antibodies are then used in a conventional quantitative immunoassay (e.g., RIA or immunohistochemical assays) to determine the amount of the gene product of interest present in a sample of proteins extracted from the tumor cells to be tested, or on the surface or at locations within the tumor cells to be tested.

In a sixth aspect, the invention provides dominant selectable markers that are useful in gene co-transfer studies. Since GSEs according to the invention confer resistance to chemotherapeutic drugs, the presence of a vector that expresses the GSE can readily be selected by growth of a vector-transfected cell in a concentration of the appropriate cytotoxic drug that would by cytotoxic in the absence of the GSE. GSEs according to the invention are particularly well suited as dominant selectable markers because their small size allows them to be easily incorporated along with a gene to be cotransfered even into viral vectors having limited packaging capacity.

In a seventh aspect, the invention provides in vivo-selectable markers that are useful both in gene therapy and in enhancing the effectiveness of chemotherapy. For gene therapy, GSEs according to the invention can be co-transferred on a vector into human CD34$^+$ blood progenitor cells from a patient along with a therapeutic gene that, when expressed, will alleviate a genetic disorder. The cells can be selected in vitro for resistance to an appropriate chemotherapeutic drug, thereby assuring successful transfer of the GSE, and by implication, of the therapeutic gene as well. The progenitor cells containing the GSE and therapeutic gene can then be returned to the patient's circulation. Finally, the cells containing the GSE and therapeutic gene can be selected in vivo by administration of the appropriate chemotherapeutic drug (to which the GSE confers resistance) in a concentration that is cytotoxic to normal blood cells. In this way, those cells having the GSE and therapeutic gene will repopulate the patient's blood.

For enhancement of chemotherapy, a GSE according to the invention can be transferred alone or with another gene on an expression vector into CD34$^+$ blood progenitor cells taken from a cancer patient. In vitro selection of the progenitor cells harboring the GSE is then carried out, using the appropriate chemotherapeutic drug. The selected cells are then returned to the patient's circulation and allowed time to begin repopulating the blood. After an appropriate period, aggressive chemotherapy can be carried out, using much higher than ordinary concentration of an appropriate chemotherapeutic drug (to which the GSE confers resistance), since toxic side effects to the immune system will be avoided due to GSE expression in those cells.

In either of these therapeutic contexts, it may be desirable to have the GSE expressed in the progenitor cells (and subsequently in the blood cells), only when its expression is beneficial, i.e., during in vitro selection of cells harboring the GSE and again during in vivo selection or chemotherapy. To accomplish this, an inducible promoter can be used to express the GSE. Then, the appropriate inducing agent is added to the cells prior to and during in vitro selection and again prior to and during in vivo selection or chemotherapy. As long as the inducing agent is not normally present in the human body, the GSE will not be expressed at any other time.

In an eighth aspect, the invention provides a starting point for the rational design of pharmaceutical products that can counteract resistance by tumor cells to chemotherapeutic drugs. The protein sequence encoded by genes from which the GSEs were derived can be deduced from the cDNA sequence, and the function of the corresponding proteins may be determined by searching for homology with known genes or by searching for known functional motives in the protein sequence. If these assays do not indicate the protein function, it can be deduced through the phenotypic effects of the GSEs suppressing the gene. Such effects can be investigated at the cellular level, by analyzing various growth-related, morphological, biochemical or antigenic changes associated with GSE expression. The GSE effects at the organism level can also be studied by introducing the corresponding GSEs as transgenes in transgenic animals (e.g. mice) and analyzing developmental abnormalities associated with GSE expression. The gene function can also be studied by expressing the full-length cDNA of the corresponding gene, rather than a GSE, from a strong promoter in cells or transgenic animals, and studying the changes associated with overexpression of the gene.

Full-length or partial cDNA sequences can also be used to direct protein synthesis in a convenient prokaryotic or eukaryotic expression system, and the produced proteins can be used as immunogens to obtain polyclonal or monoclonal antibodies. These antibodies can be used to investigate the protein localization and as specific inhibitors of the protein function, as well as for diagnostic purposes. In particular, antibodies raised against a synthetic peptide encoded by part of the complement of the sequence of the GSE anti-khcs, or the corresponding region of the human KHCS protein should be particularly useful, as should antibodies raised against an amino acid sequence encoded by part of the VPA or VP9-11 GSEs (see FIGS. 9–11).

Understanding the biochemical function of a gene involved in drug sensitivity is likely to suggest pharmaceutical means to stimulate or mimic the function of such a gene and thus augment the cytotoxic response to anticancer drugs. For example, if the gene encodes an enzyme producing a certain compound, such a compound can be synthesized chemically and administered in combination with cytotoxic drugs. If a pharmaceutical approach is not apparent from the protein function, one may be able to upmodulate gene expression at the level of transcription. This can be done by cloning the promoter region of the corresponding gene and analyzing the promoter sequence for the presence of cis elements known to provide the response to specific biological stimulators.

The most straightforward way to increase the expression of a drug sensitivity gene, identified through the GSE approach, would be to insert a full-length cDNA for such a gene into a retroviral vector. Such a vector, in the form of a recombinant retrovirus, will be delivered to tumor cells in vivo, and, upon integration, would sensitize such cells to the effects of the corresponding chemotherapeutic drug. A similar strategy for selective delivery of a drug-sensitivity gene into rat brain tumors, followed by curative treatment with the appropriate drug, was reported by Culver et al., Science 256:1550–1552 (1992). The selective delivery to tumor cells can be accomplished on the basis of the selectivity of retrovirus-mediated transduction for dividing cells. Alternatively, the selectivity can be achieved by driving the expression of the drug sensitivity gene from a tissue- or tumor-specific promoter, such as, for example, the promoter of the carcinoembryonic antigen gene.

The protein structure deduced from the cDNA sequence can also be used for computer-assisted drug design, to develop new drugs that affect this protein in the same manner as the known anticancer drugs. The purified protein, produced in a convenient expression system, can also be used as the critical component of in vitro biochemical screening systems for new compounds with anticancer activity. Accordingly, mammalian cells that express chemotherapeutic drug resistance-conferring GSEs according to the invention are useful for screening compounds for the ability to overcome drug resistance.

The following examples are intended to further illustrate certain preferred embodiments of the invention and are not limiting in nature.

EXAMPLE 1

Development of GSEs for Human Topoisomerase II

Topoisomerase II is a DNA unwinding enzyme that serves as a target for many anti-cancer drugs, including etoposide, doxorubicin and amsacrine. The enzyme normally acts by double-strand DNA cleavage, followed by strand passage and religation of the breaks. Anti-cancer drugs cause trapping of the enzyme in complexes having double-strand breaks held together by the enzyme, thereby leading to lethal damage in replicating cells. Some cell lines that are resistant to anti-cancer drugs that interact with topoisomerase II have decreased expression of this enzyme.

Random fragment selection of GSEs requires transfer of the expression library into a very large number of recipient cells. Therefore, to prepare a random fragment library containing GSEs for topoisomerase II, the efficient retroviral vector system was chosen. Overlapping cDNA clones spanning the entire coding sequence for topoisomerase II were mixed and randomly fragmented into 250–350 bp fragments by DNase I in the presence of $Mn^{++}$ ions and fragment termini were filled in with T4 DNA polymerase and Klenow fragment of DNA polymerase I. After ligation with a synthetic adaptor providing translation initiation and termination codons, the fragment mixture was amplified by PCR, using adaptor-derived primers. The amplified mixture was cloned into the LNCX retroviral vector which contains a neo gene. (see Miller and Rosman, Biotechniques 7:980–986 (1989)).

A random fragment library containing 20,000 independent clones was obtained, and was used to transfect amphotropic and ecotropic virus-packaging cell lines derived from NIH 3T3 cells, to effect ping-pong replication-mediated amplification of the virus (e.g., see Bodine, et al. Proc. Natl. Acad. Sci. USA 87:3738–3742 (1990)). This resulted in a random fragment expression library (RFEL), a set of recombinant retroviruses containing a representative mixture of inserts derived from topoisomerase II gene sequences.

The uniformity of sequence representation in RFEL was monitored as follows. NIH 3T3 cells were infected with virus-containing supernatant, followed 24 hours later by PCR amplification of integrated proviral insert sequences in the presence of $[^{32}P]$ alpha-dNTP. An aliquot of the PCR-amplified mixture was subjected to gel electrophoresis to establish the absence of predominant bonds. Another aliquot was used as a probe for a Southern blot of topoisomerase II cDNA digested with several frequently cutting restriction enzymes. A representative sequence mixture was obtained, as evidenced by the absence of a predominant band in the first test, and uniform hybridization to all fragments in the second test.

RFEL was then used to infect HeLa cells, and the infectants were selected with G418. Colonies of G418-resistant cells, having about 50–70 cells each, were then exposed to etoposide at a concentration of 200 μg/ml. Approximately 50 to 10,000 G418-resistant colonies were etoposide resistant, compared to a frequency of $<10^{-4}$ when insertless retroviruses were used as a control. Cell lines were isolated from etoposide-resistant colonies. Amphotropic and ecotropic packaging cell lines producing RFEL were also selected for etoposide resistance. Virus from etoposide resistant packaging cell lines were used to infect HeLa cells, which were then selected with G418. G418-resistant infectants were challenged with three topoisomerase II-interactive anticancer drugs: etoposide, teniposide and amsacrine. A high proportion of infected cells were resistant to all three drugs, thus demonstrating that etoposide selection of mouse packaging cell lines has led to the generation of GSEs active in both human and mouse cells. These infectants were also used to establish cell lines. RFEL-derived inserts were recovered from etoposide resistant cell lines by PCR and recloned into LNCX vector. The newly-derived clones were then individually tested for the ability to confer resistance to etoposide upon transfection into HeLa cells, to confirm the GSE activity of the corresponding inserts.

Sequence analysis of 26 different isolated clones related that 16 of them were inserted in antisense and 10 in sense orientation. Of the 12 GSEs confirmed, 7 were sense and 5 antisense, as shown in Table I. The sequences of the confirmed GSEs are shown in FIGS. 1A through 1L. The sense-oriented inserts of the confirmed GSEs encode 37–99 amino acid long topo II-derived peptides, initiating either from the ATG codon provided by the adaptor, or from an internal ATG codon within the open reading frame of Topoisomerase II, located close to the 5' end of the insert in an appropriate context for translation initiation. Four of the confirmed antisense GSEs come from the 3' third of the cDNA and one from the 5' end of cDNA, including the translation start site. Of the sense-oriented GSEs, five are derived from the central portion of the protein that includes the active site tyrosine-804 that covalently binds to DNA and the "leucine zipper" region involved in dimerization of Topoisomerase II. One GSE peptide is derived from the region near the N-terminus and another from the region near the C-terminus of the protein; no known functional sites are associated with either segment.

TABLE I

Confirmed Topoisomerase II-Derived GSE

| Clones | Orientation (Sense/Antisense) | Position in cDNA[a] | Position of peptide[b] |
|---|---|---|---|
| 2V | Antisense | −18–145 | |
| Σ11 | Sense | 393–605 | 134–201 |
| 6 | Sense | 2352–2532 | 808–844 |
| 5 | Sense | 2511–2734 | 846–911 |
| Σ28 | Sense | 2603–2931 | 879–977 |
| Σ2 | Antisense | 3150–3343 | |
| Σ20 | Antisense | 3486–3692 | |
| 39 | Antisense | 3935–4127 | |
| 12S | Sense | 4102–4343 | 1368–1447 |
| ΣVPs2 | Sense | 2494–2834 | 846–944 |
| Σ8 | Antisense | 4123–4342 | |
| ΣVM | Sense | 2501–2670 | 846–890 |

[a]Position in the cDNA sequence of topoisomerase II; residues numbered as in Tsai-Pflugfelder et al., Proc. Natl. Acad. Sci. USA 85:7177–7181 (1988).
[b]Position of the peptide encoded by sense-oriented GSEs in the amino acid sequence of topoisomerase II; translation assumed to initiate from the first ATG codon in the correct open reading frame.

These results demonstrate that GSEs that act according to multiple mechanisms to confer etoposide resistance can be prepared from a random fragment library of DNA encoding topoisomerase II. In addition, these results show that GSEs produced from one mammalian species can be active in another mammalian species.

EXAMPLE 2

Generation of a Normalized Random Fragment cDNA Library in a Retroviral Vector

Figure 2B:
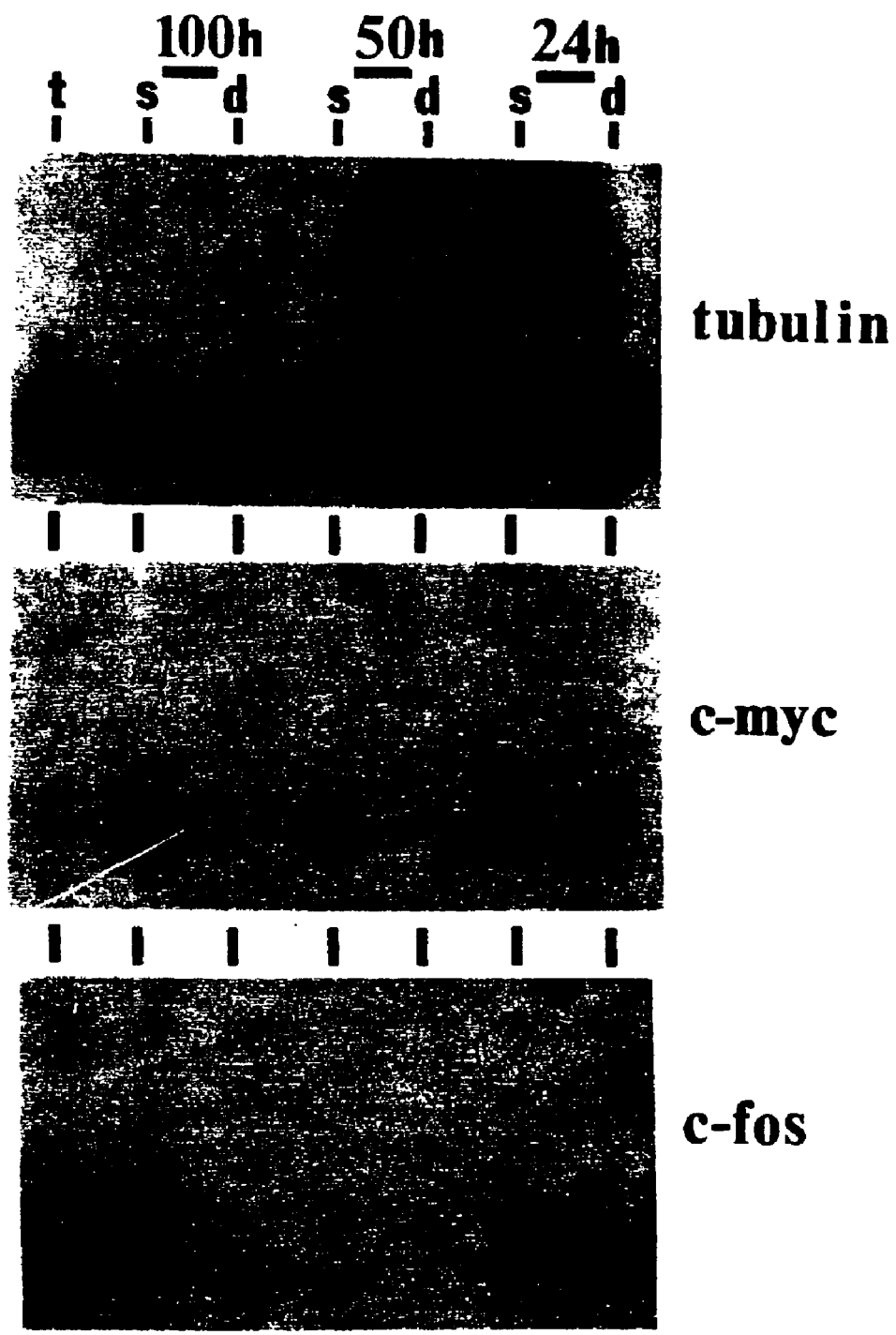

As shown in FIGS. 2A and 2B a normalized cDNA population was prepared using a modification of the protocol of Patanjali et al., Proc. Natl. Acad. Sci. USA 88:1943–1947 (1991). Poly(A)$^+$ RNA was extracted from NIH 3T3 cells. To obtain mRNAs for different genes expressed at various stages of the cell growth, one half of the RNA was isolated from a rapidly growing culture and the other half from quiescent cells that had reached complete monolayer confluency. To avoid overrepresentation of the 5'-end sequences in a randomly primed cDNA population, RNA was fragmented by boiling to an average size range 600–1,000 nucleotides. These RNA fragments were then used for preparing randomly primed double-stranded cDNA. This randomly primed cDNA was then ligated to a synthetic adaptor providing ATG codons in all three possible reading frames and in a proper context for translation initiation. The structure of the adaptor (see FIG. 3B) determined its ligation to the blunt-ended fragments of the cDNA in such a way that each fragment started from initiation codons independently from its orientation. The adaptor was not supplied with termination codons in the opposite strand since the cloning vector pLNCX, contained such codons immediately downstream of the cloning site. This vector has been described by Miller and Rosman, Biotechniques 7:980–986 (1989). The ligated mixture was amplified by PCR, using the "sense" strand of the adaptor as a PCR primer, in contrast to the method of Patanjali et al., which utilized cloning the initial cDNA preparation into a phage vector and then using vector-derived sequences as PCR primers to amplify the cDNA population. The PCRs were carried out in 12 separate reactions that were subsequently combined, to minimize random over- or under-amplification of specific sequences and to increase the yield of the product. The PCR-amplified mixture was size-fractionated by gel electrophoresis, and 200–500 bp fragments were selected for subsequent manipulations in contrast to Patanjali's fragment size range of from 400 to 1,600 bp.

For normalization, the cDNA preparation was denatured and reannealed, using different time points, as described by Patanjali et al., supra, and shown in FIGS. 2A and 2B, for reannealing. The single-stranded and double-stranded DNAs from each reannealed mixture were separated by hydroxyapatite chromatography. The single-stranded DNA fractions from each time point of reannealing were PCR-amplified using the adapter-derived primer and analyzed by Southern hybridization for the relative abundance of different mRNA sequences. The fraction that contained similar proportions of tubulin, c-myc and c-fos cDNA sequences (see FIGS. 2A and 2B), corresponding to high-, medium- and low-expressed genes, respectively, was used for the library preparation.

Figure 3A:
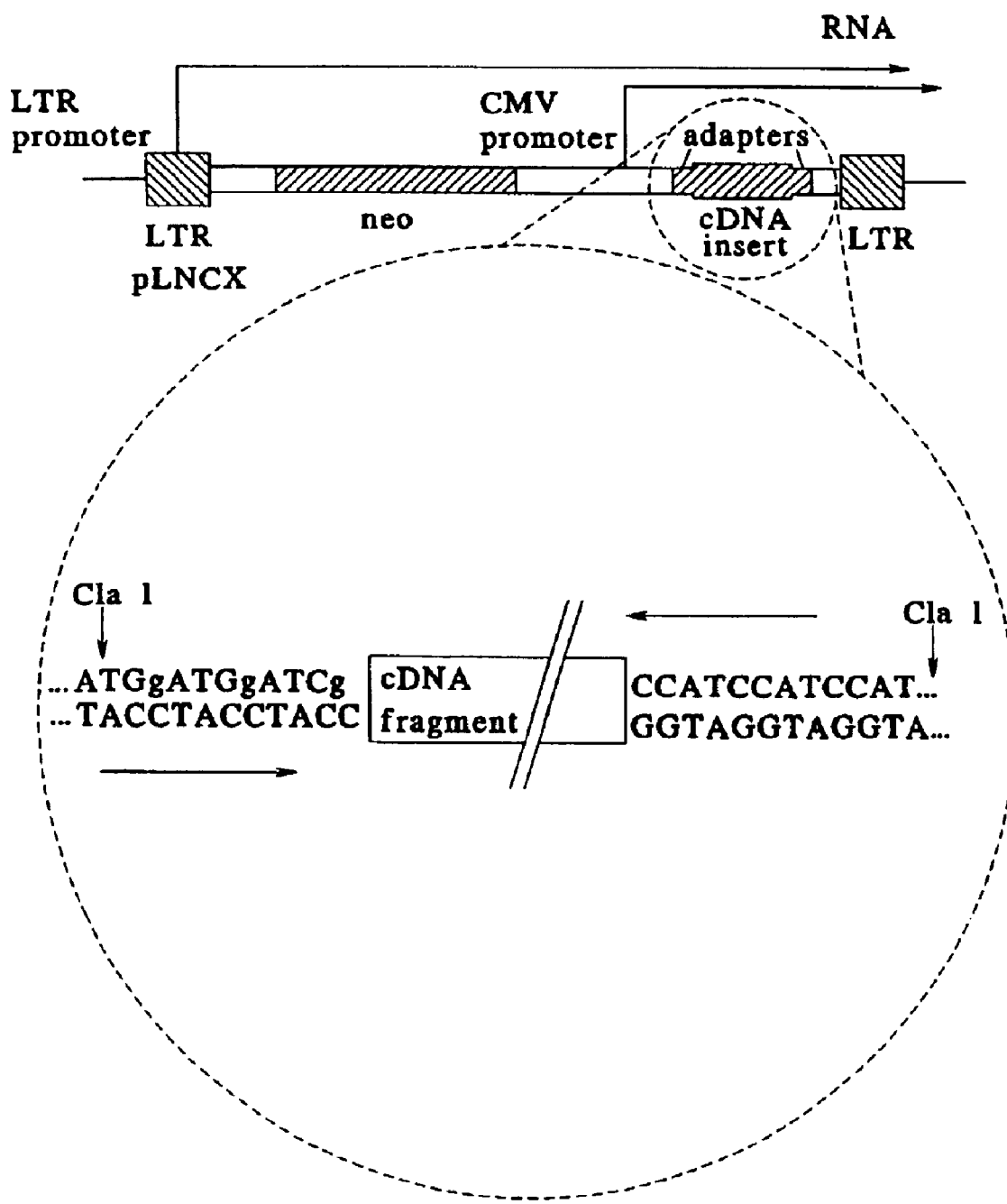
FIGS. 3A and 3B shows the structure of the LNCX vector and the adaptor used for cDNA cloning. The nucleotide sequences are shown for the ATG-sense [SEQ. ID. NO. 13] and ATG-antisense [SEQ. ID. NO. 14] strands of the adaptor.
Figure 3B:
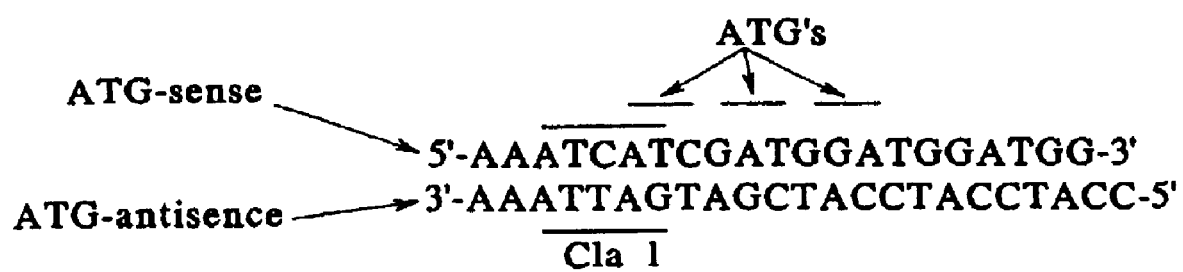

The normalized cDNA preparation was cloned into the Cla I site of the MoMLV-based retroviral vector pLNCX, which carries the neo (G418 resistance) gene, transcribed from the promoter contained in the retroviral long terminal repeat (LTR), and which expresses the inserted sequences from a strong promoter of the cytomegalovirus (CMV) (see FIG. 3A). The ligation mixture, divided into five portions, was used for five subsequent large-scale transformations of E.coli. The transformed bacteria were plated on the total of 500 agar plates (150 mm in diameter) and the plasmid population (18 mg total) was isolated from the colonies washed off the agar. A total of approximately $5 \times 10^7$ clones were obtained, more than 60% of which carried the inserts of normalized cDNA, as estimated by PCR amplification of inserts from 50 randomly picked colonies. These results demonstrate the feasibility of generating a normalized cDNA library of as many as $3 \times 10^7$ recombinant clones in a retroviral plasmid expression vector.

EXAMPLE 3

Transduction of a Retroviral Random Fragment Library into Virus-Packaging Cell Lines and NIH 3T3 Cells The plasmid library prepared according to Example 2 was converted into a mixture of retroviral particles by transfection into virus-packaging cells (derivatives of NIH 3T3) that express retroviral virion proteins. Examples of such cell lines have been described by Markowitz et al., Virology 167:400–406 (1988). Ecotropic and amphotropic virus-packaging cell lines, GP+E86 and GP+envAm12, respectively, were mixed at a 1:1 ratio, and $10^7$ cells of this mixture were transfected with the plasmid library under standard calcium phosphate coprecipitation conditions. This transfection resulted in the packaging and secretion of ecotropic and amphotropic virus particles, which rapidly spread through the packaging cell population, since ecotropic viruses are capable of infecting amphotropic packaging cells and vice versa. The yield of the virus, as measured by the number of G418-resistant colonies obtained after the infection of NIH 3T3 cells, reached $10^5$ infectious units per 1 ml of media during the stage of transient transfection (1–3 days), then decreased (4–8 days) and then rapidly increased due to the expression of proviral genomes that became stably integrated in most of the packaging cells. The yield of the virus 9–12 days after transfection reached >$10^6$ per 1 ml of media supernatant. At this stage, the library showed fairly even representation of different fragments, but at later stages individual virus-producing clones began to predominate in the population, leading to uneven representation of cDNA-derived inserts. The uniformity of sequence representation in the retroviral population was monitored by rapid extraction of DNA from cells infected with the virus-containing supernatant, followed by PCR amplification of inserts. The inserts were analyzed first by the production of a continuous smear in the ethidium-bromide stained agarose gel and then by Southern hybridization with different probes, including topisomerase II, c-myc and tubulin. As long as each gene was represented by a smear of multiple fragments, the representativity of the library was considered to be satisfactory.

In other experiments, for transducing the random-fragment normalized cDNA library into NIH 3T3 cells, without loss of representativity, NIH 3T3 cells were infected either with a virus produced at the transient stage of transfection (days 1–3), or with the high-titer virus collected 10–12 days after transfection. In the latter case, 100 ml of viral suspension contained more than $10^8$ infectious units. In the case of the "transient" virus, NIH 3T3 cells were infected with at least $10^7$ recombinant retroviruses by using 500 ml of media from virus-producing cells (five rounds of infection, 100 ml of media in each). These results demonstrate the feasibility of converting a large and complex random fragment library into retroviral form and delivering it to a non-packaging cell line without loss of complexity.

EXAMPLE 4

Isolation of GSEs Conferring Resistance to the Chemotherapeutic Drug Etoposide

Figure 4:
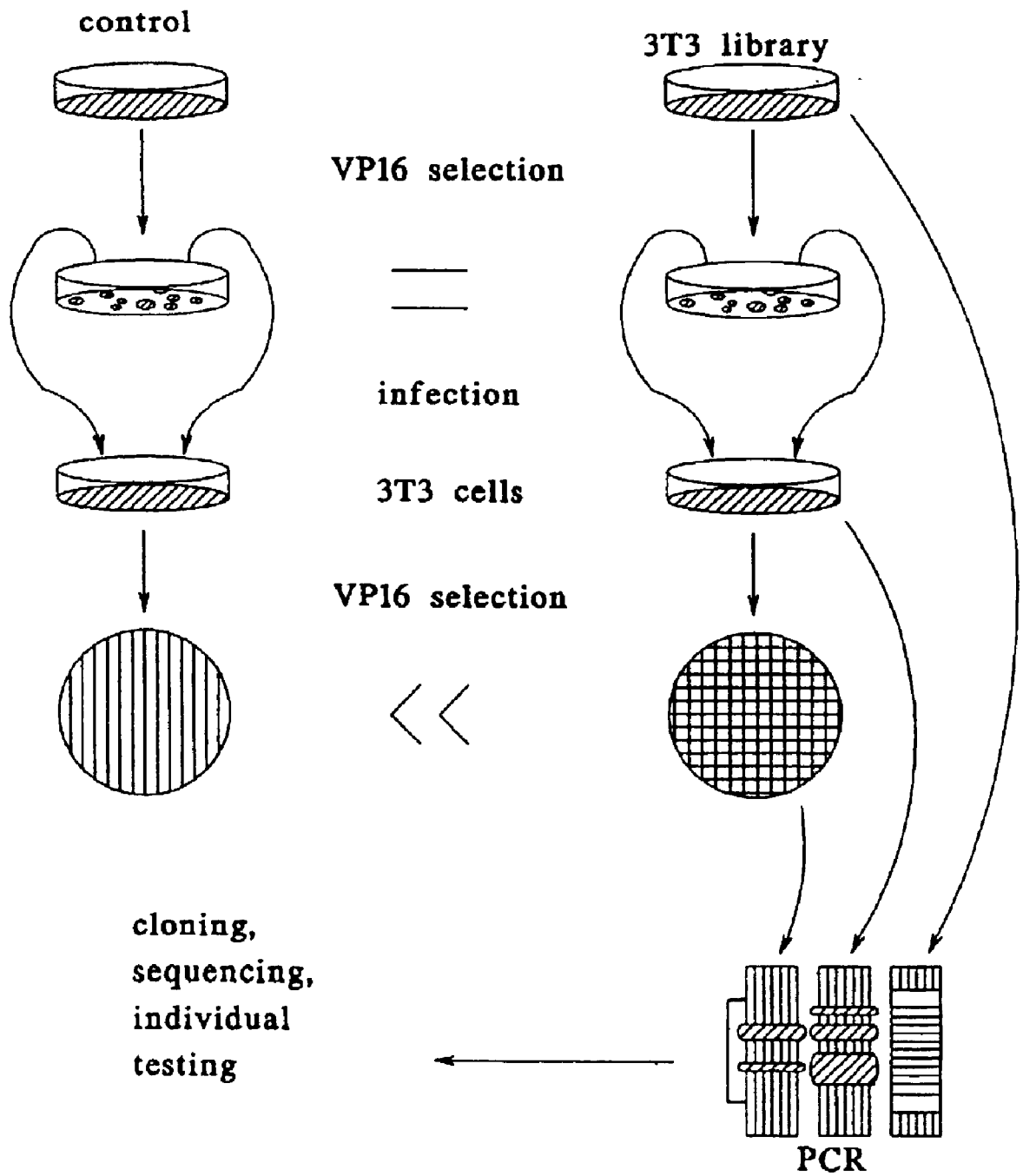
FIG. 4 shows the overall scheme for selecting cell lines containing chemotherapeutic drug resistance-conferring GSEs and rescuing the GSEs from these cells.
Figure 5B:

The overall scheme for the selection of GSEs conferring etoposide resistance is illustrated in FIG. 4. This selection was carried out directly on virus-producing packaging cells, in the expectation that cells whose resistant phenotype is caused by the GSE expression will provide virus particles carrying such a GSE. The mixture of amphotropic and ecotropic packaging cells was transfected with the cDNA library in the LNCX vector, prepared according to Example 2 and the virus was allowed to spread through the population for 9 days. Analysis of a small part of the population for G418 resistance showed that practically 100% of the cells carried the neo-containing provirus. The cells were then exposed to 350 ng/ml etoposide for 15 days and then allowed to grow without drug for two more weeks. No difference was observed between the numbers of colonies obtained in the experiment and in the control (uninfected cells or cells infected with the insert-free LNCX virus) after etoposide selection. The virus present in the media supernatant of the surviving cells was then used to infect NIH 3T3 cells followed by etoposide selection using essentially the same protocol. NIH 3T3 cells infected with the library-derived virus produced by packaging cells that were selected with etoposide showed a major increase in the number of etoposide-resistant cells relative to the control cells infected with the insert-free LNCX virus, indicating the presence of biologically active GSEs in the preselected virus population (see FIG. 5A).

Figure 6:
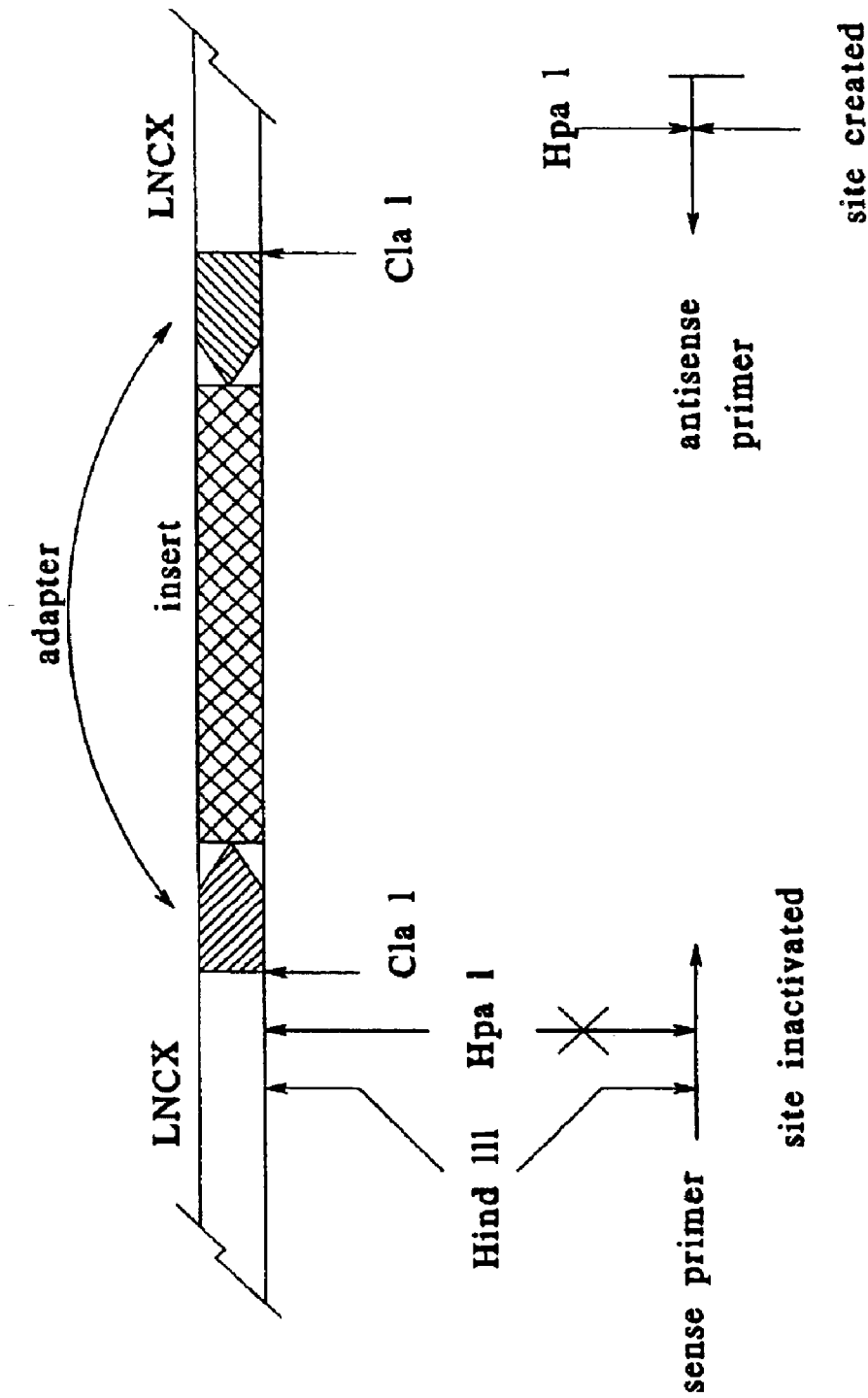
FIG. 6 shows a scheme for recloning individual PCR-amplified fragments from etoposide resistant selected cells into the LNCX vector, as described in Example 4.
Figure 7A:
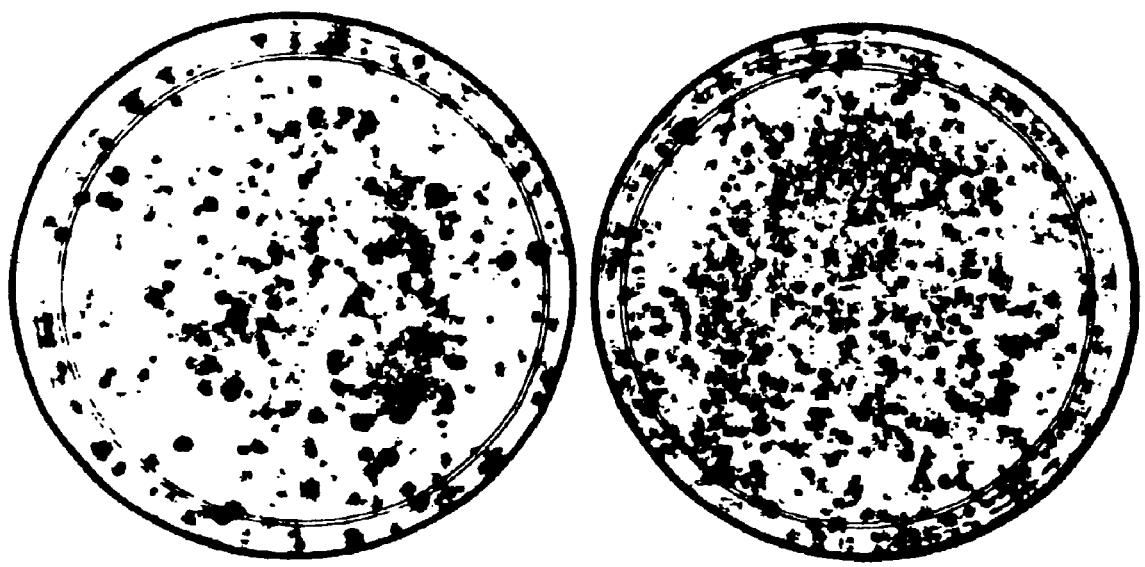
FIGS. 7A and 7B demonstrate resistance to 350 ng/ml etoposide, conferred upon the cells by the GSEs VPA FIG. 7A and VP9-11 FIG. 7B.
Figure 7B:
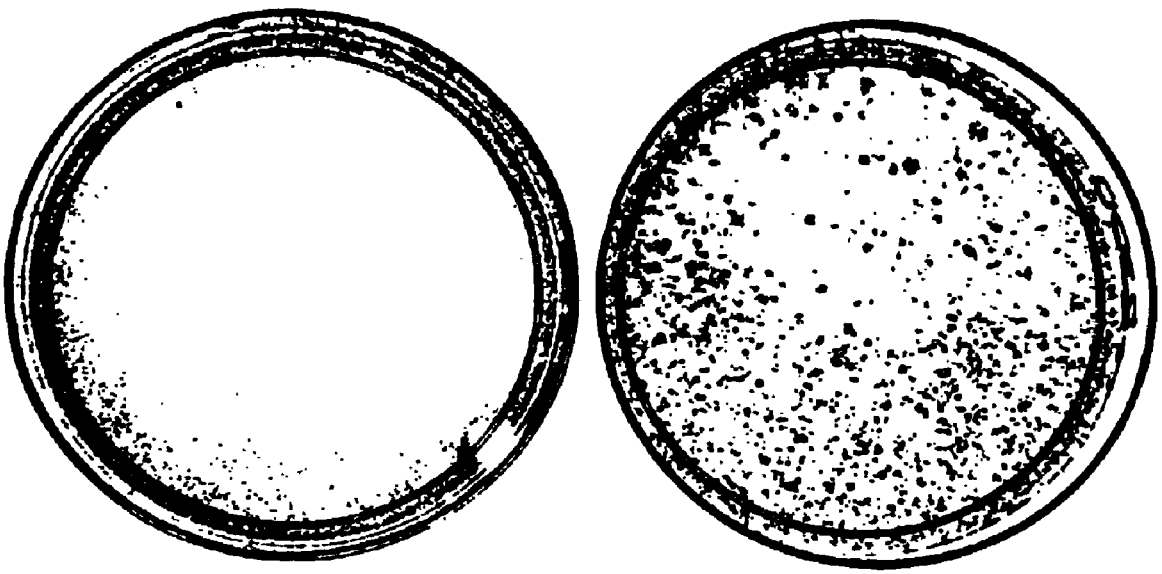
Figure 8B:
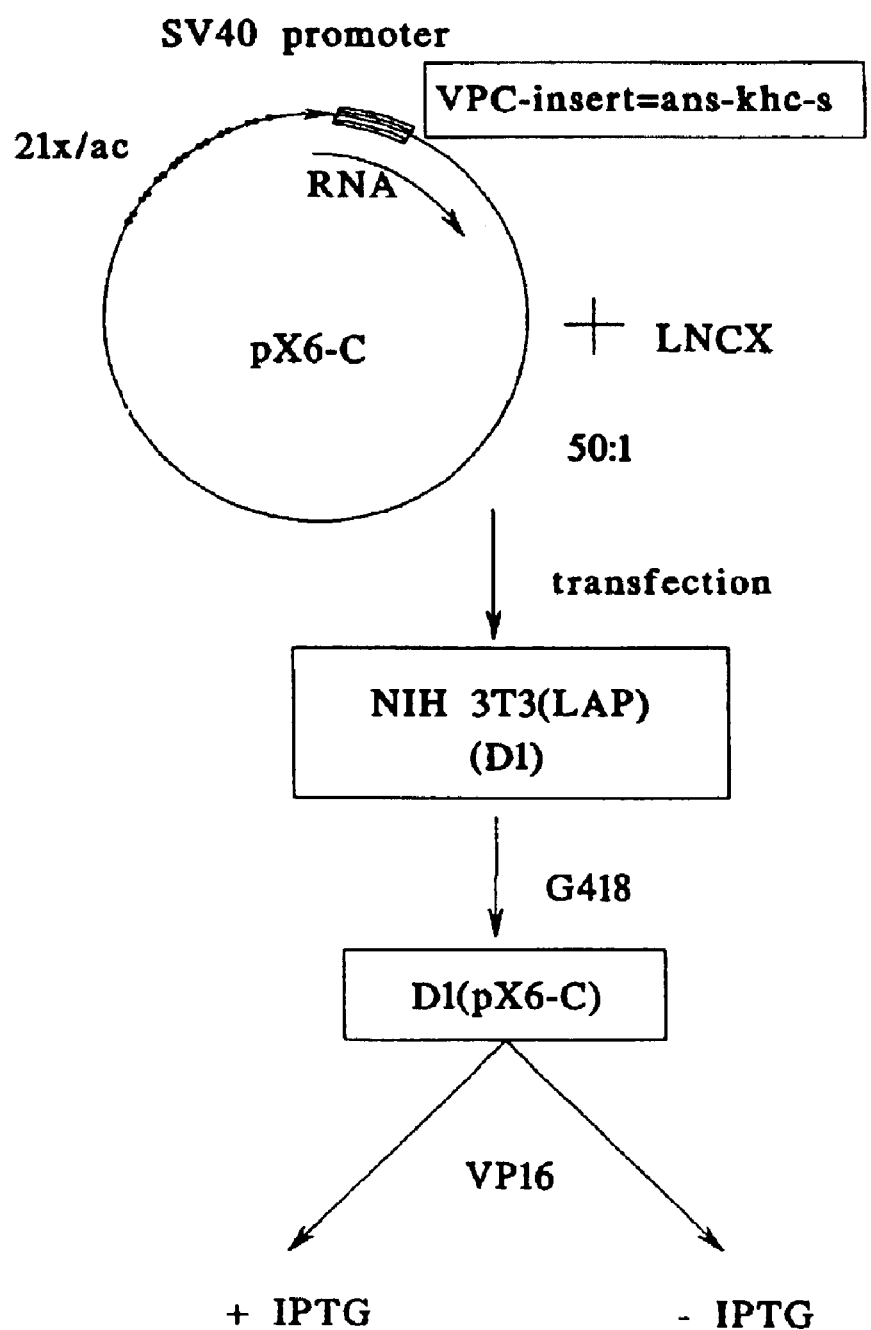
Figure 13A:
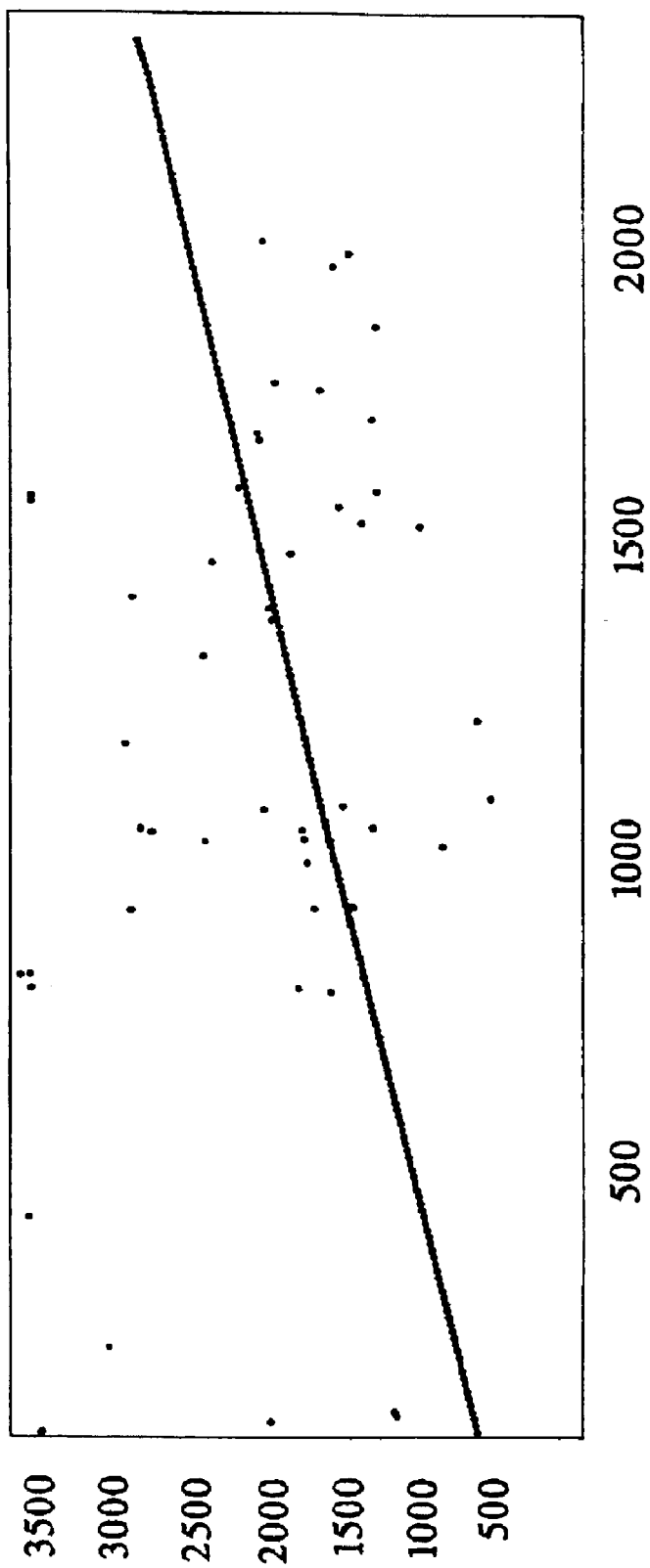
FIGS. 13A through 13D shows the dot matrix alignments of khcs protein sequence deduced from the nucleotide sequence in FIG. 12 with kinesin heavy chain sequences from human FIG. 13A, mouse FIG. 13B, squid FIG. 13C or the portion of mouse khcs encoded by the anti-khcs GSE FIG. 13D.
Figure 13B:
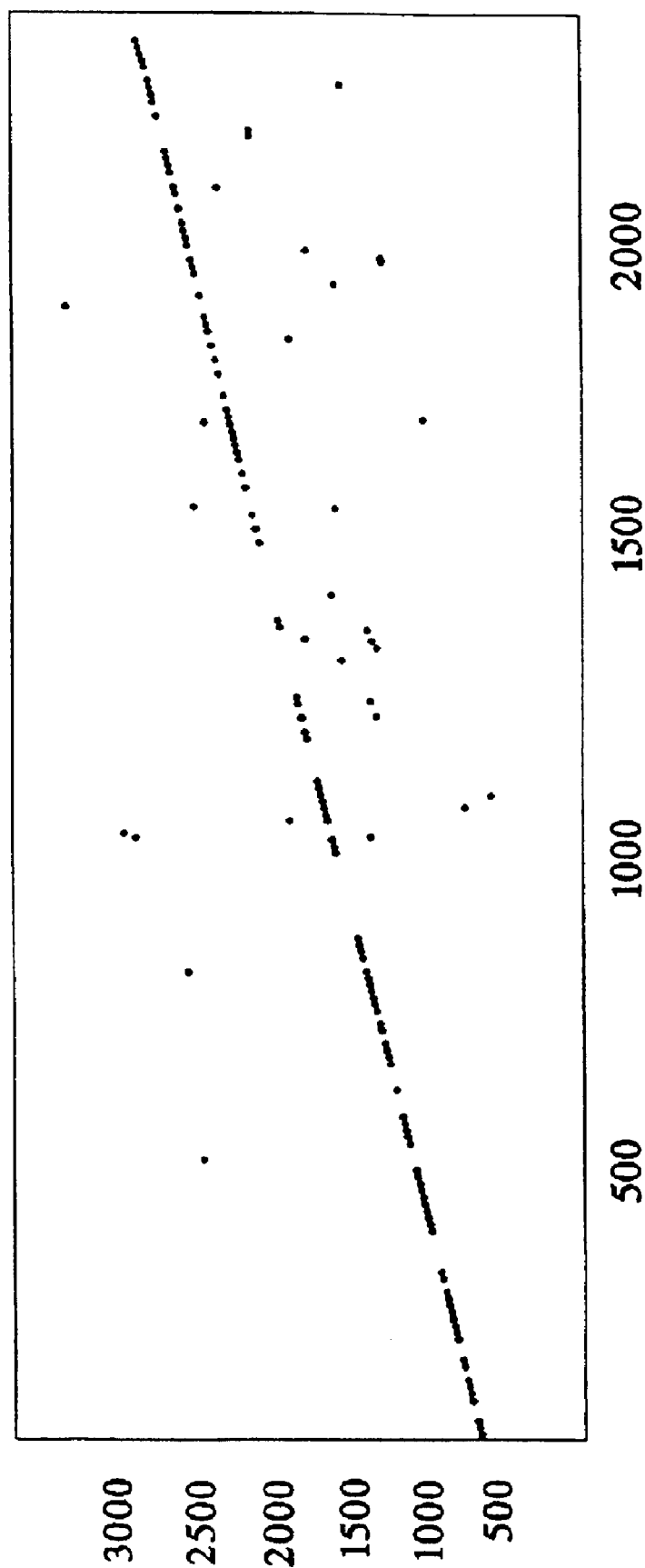
Figure 13C:
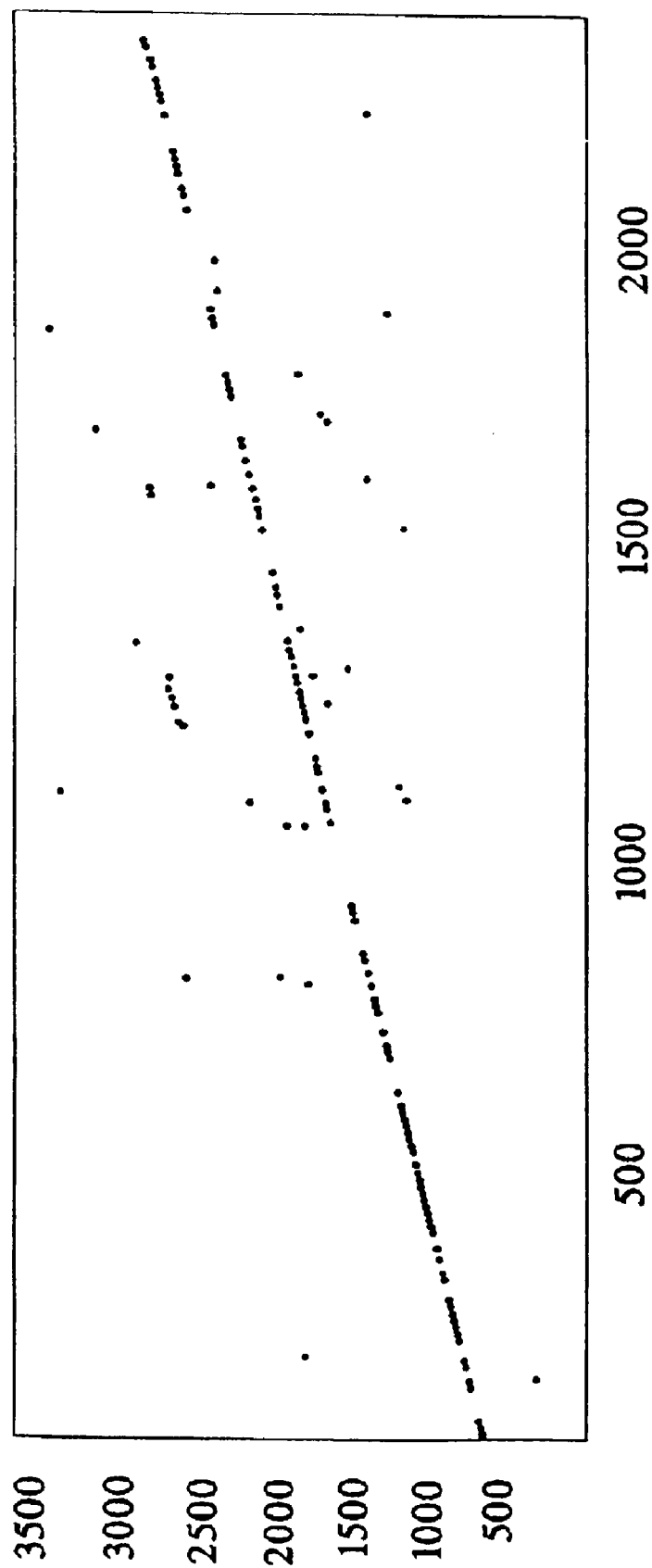
Figure 13D:
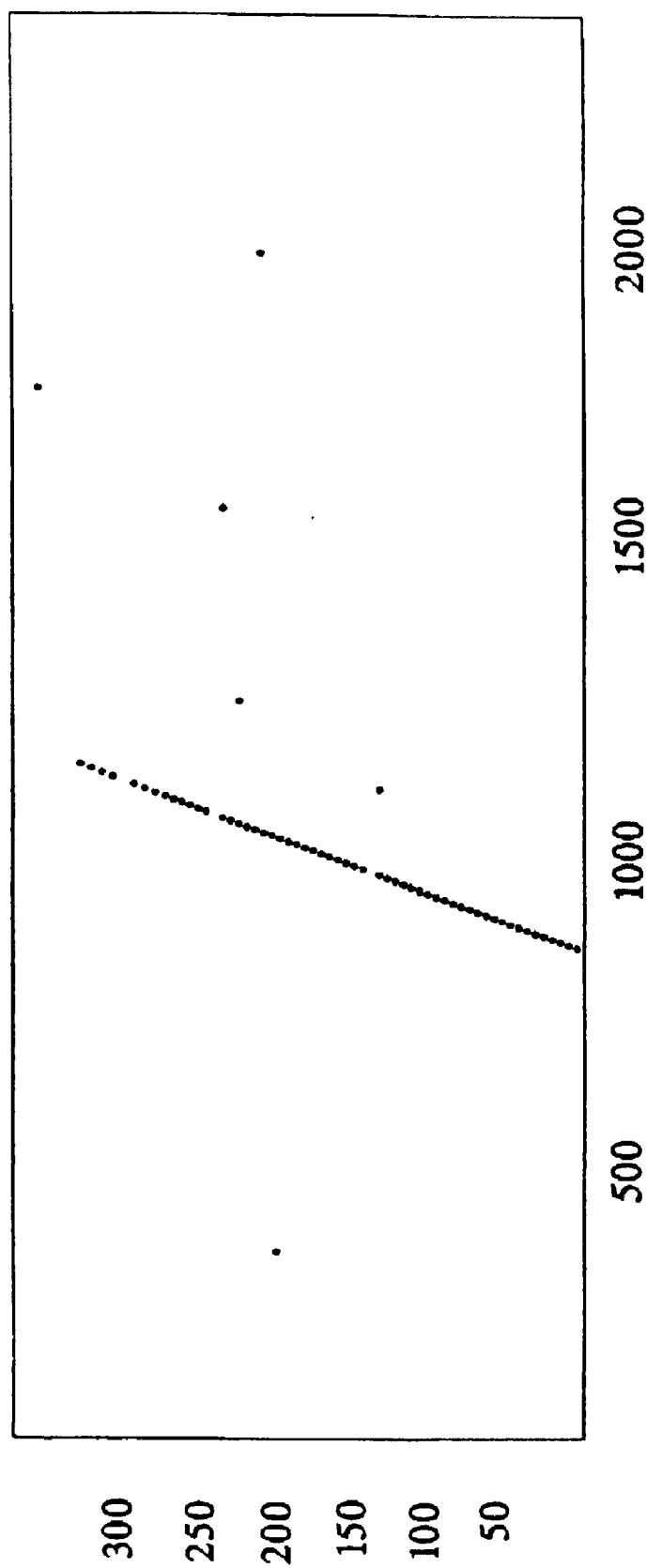
Figure 14A:
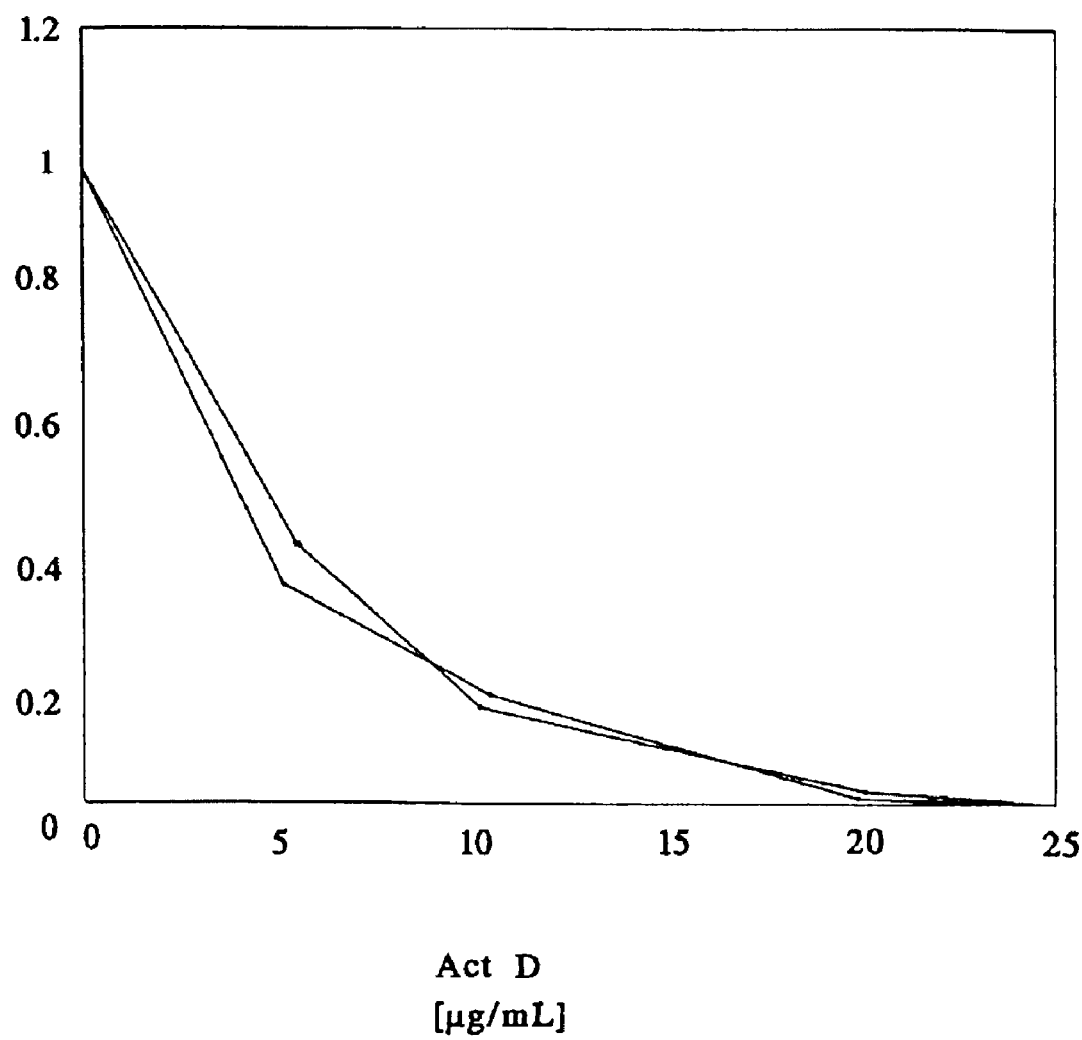
FIGS. 14A through 14F shows the plating efficiency in the presence of various chemotherapeutic drugs of NIH 3T3 cells infected with the LNCX vector (indicated by crosses) or with the LNCX vector containing the anti-khcs GSE (indicated by dots).
Figure 14B:
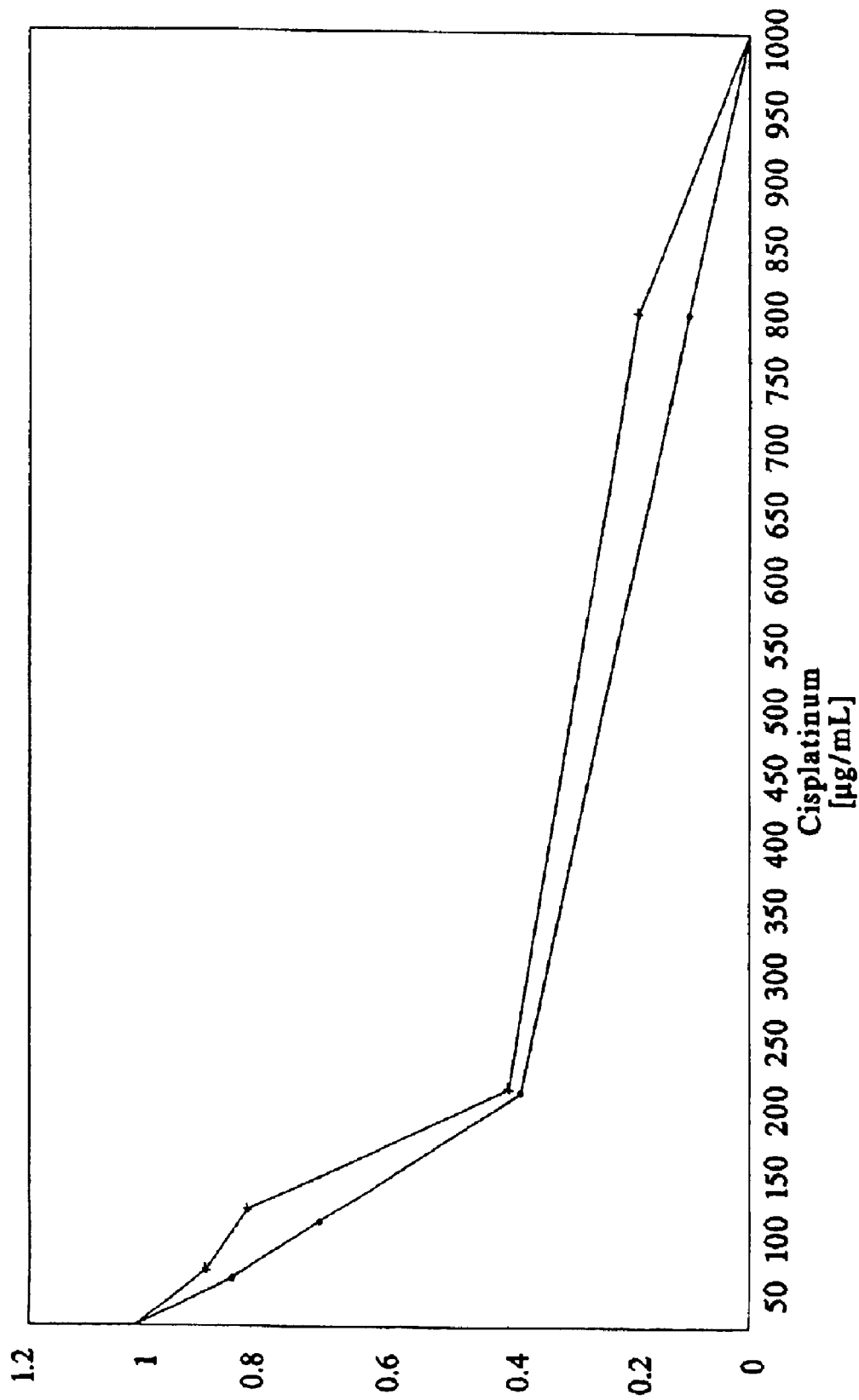
Figure 14C:
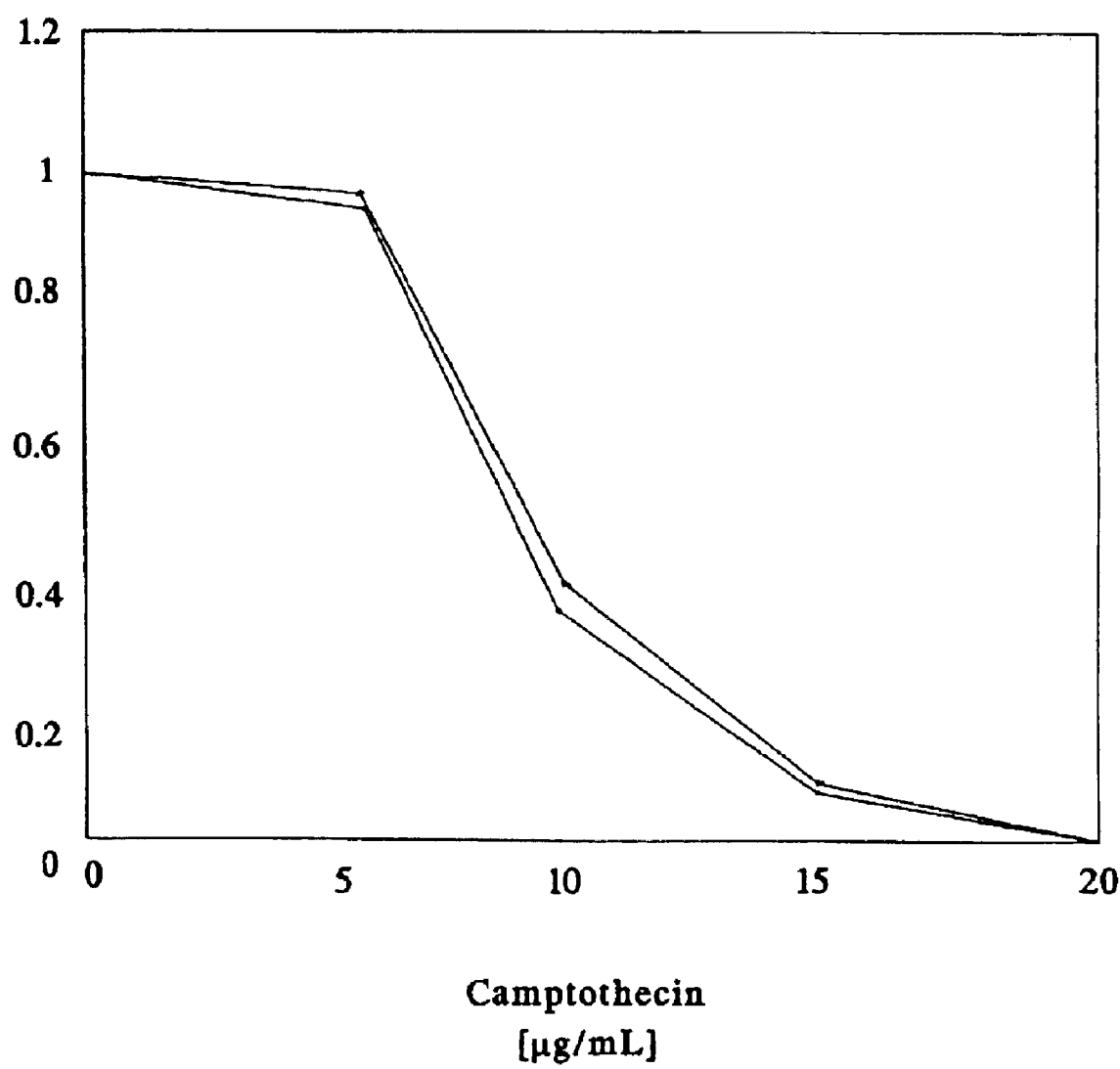
Figure 14D:
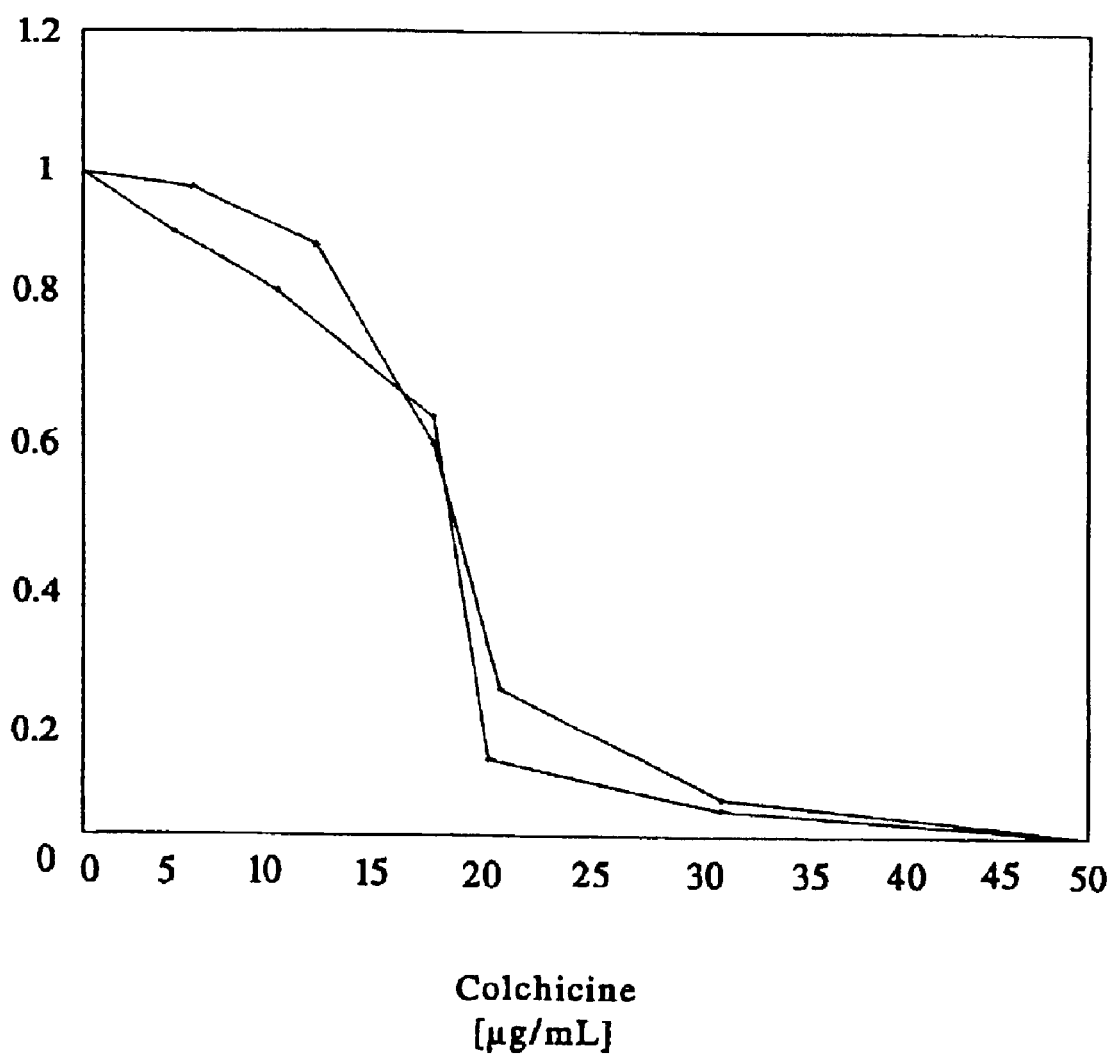
Figure 14E:
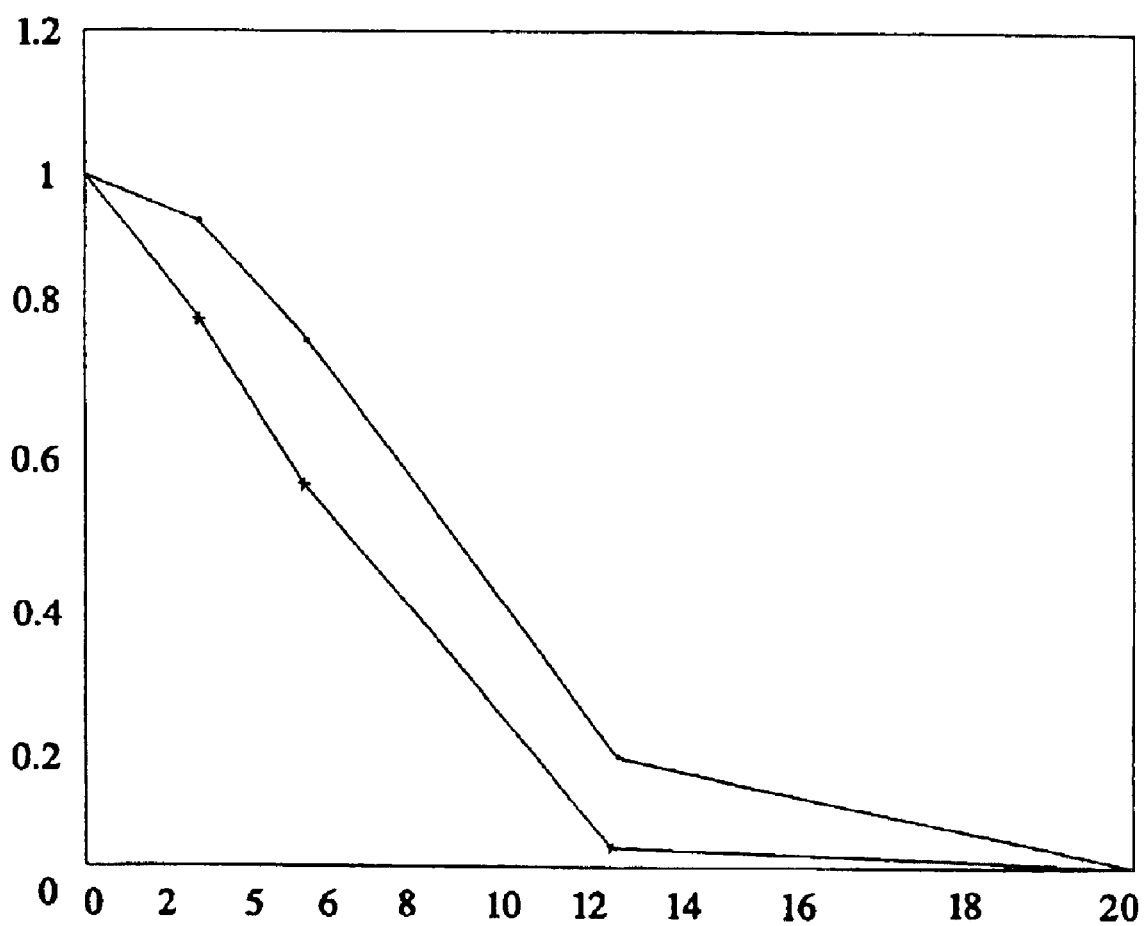
Figure 14F:
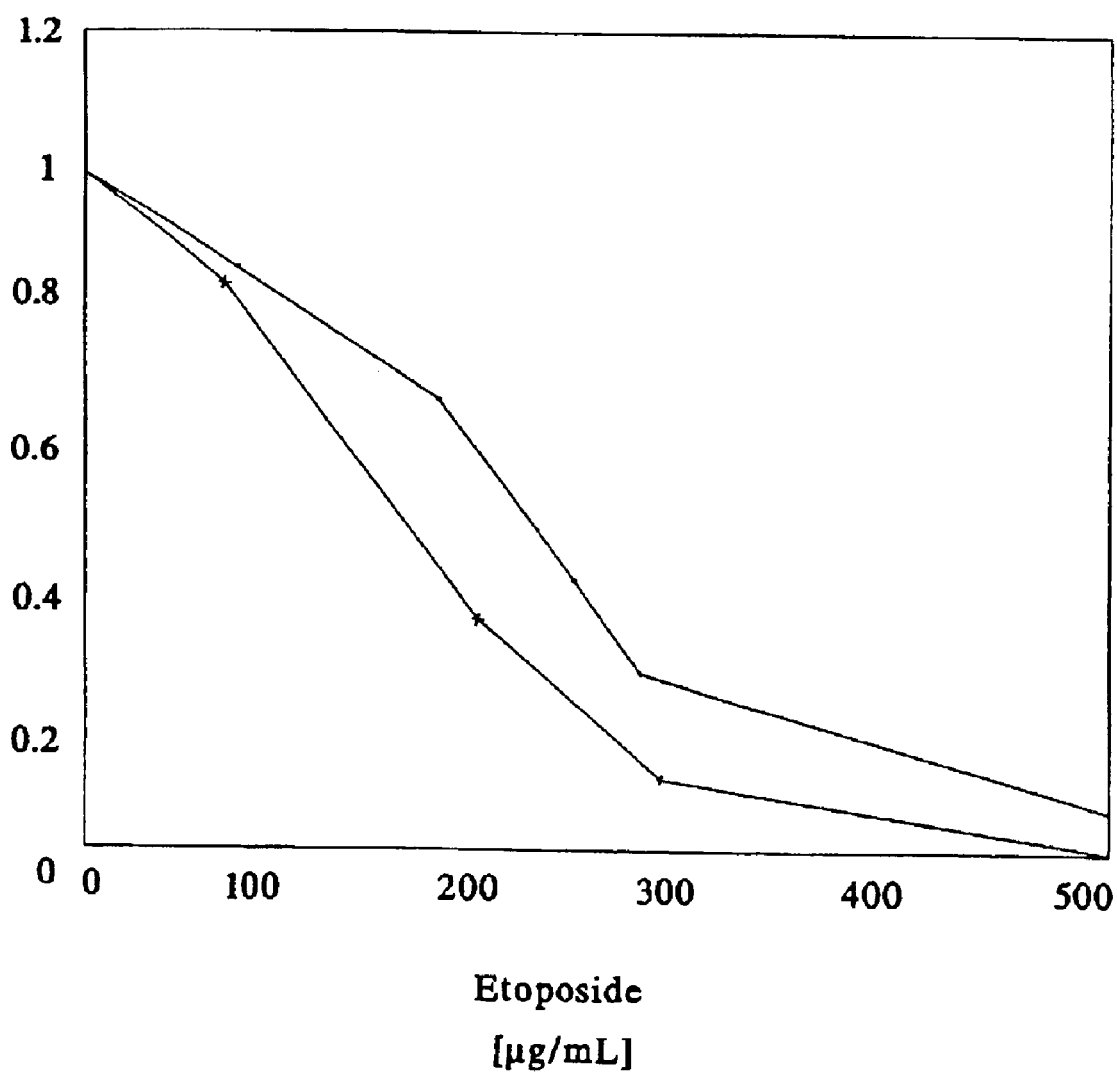

The proviral inserts contained in the etoposide-selected NIH 3T3 cells were analyzed by PCR. This analysis (see FIG. 5B) showed an enrichment for specific fragments, relative to the unselected population of the infected cells. Individual PCR-amplified fragments were recloned into the LNCX vector in the same position and orientation as in the original plasmid, as illustrated in FIG. 6. A total of 42 proviral inserts, enriched after etoposide selection, were thus recloned, and tested either in batches or individually for the ability to confer increased etoposide resistance after retroviral transduction into NIH 3T3 cells. Three non-identical clones were found to induce etoposide resistance, indicating that they contained biologically active GSEs. Etoposide resistance induced by these clones is illustrated in FIGS. 7A and 7B and FIGS. 8A and 8B. These GSEs were named anti-khcs VPA and VP9-11.

The ability of one of these GSEs (anti-khcs) to induce etoposide resistance was further documented by using the isopropyl β-D-thiogalactopyranoside (IPTG)-inducible promoter/activator system, as described by Baim et al., Proc. Natl. Acad. Sci. USA 88:5072–5076 (1991). The components of this system include an enhancer-dependent promoter, combined in cis with multiple repeats of the bacterial lac operator, and a gene expressing LAP267, an artificial regulatory protein derived from the lac repressor and a mammalian transcriptional activator. The anti-khcs GSE was cloned into the plasmid pX6.CLN, which contains the inducible promoter used by Baim et al., supra, (a gift of Dr. T. Shenk) which expresses the inserts from an enhancer-less SV40 early gene promoter supplemented with 21 repeats of the lac operator sequence. The resulting plasmid, which contains no selectable markers, was co-transfected into NIH 3T3 cells together with the LNCX plasmid carrying the neo gene. The mass population of G418-selected transfectants, along with control cells transfected with the insert-free vector, was exposed to increasing concentrations of etoposide, in the presence or in the absence of 5 mM IPTG. Even though the co-transfection protocol usually leads to the integration of the GSE in only a fraction of the G418-resistant cells, transfection with anti-khcs resulted in a clearly increased etoposide resistance, which was dependent on IPTG (see FIGS. 8A and 8B).

EXAMPLE 5

Sequence Analysis of GSEs Conferring Resistance to the Chemotherapeutic Drug Etoposide The GSEs anti-khcs, VPA, and VP9-11, cloned as described in Example 4, were sequenced by the standard dideoxy sequencing procedure, and the deduced sequences are shown in FIGS. 9–11. The nucleotide sequences of the "sense" and "antisense" strands, as well as amino acid sequences of the peptides encoded by these strands, were analyzed for homology to the nucleic acid and protein sequences present in the National Center for Biotechnology Information data base, using the BLAST network program for homology search. No significant homology with any sequence was deleted for the GSEs VPA and VP9-11. In contrast, the sequence corresponding to the "antisense" strand of the anti-khcs GSE, showed strong homology with several genes encoding the heavy chain of kinesins, a family of microtubule motor proteins involved in intracellular movement of organelles or macromolecules along the microtubules of eukaryotic cells. This protein family has been reviewed by Endow, Trends Biochem. Sci. 16:221–225 (1991). The highest homology was found with the human kinesin heavy chain (KHC) gene, as described by Navone et al., J. Cell Biol. 117:1263–1275 (1992). Anti-khcs therefore encodes antisense RNA for a mouse khc gene, which we term khcs for khc associated with sensitivity (to drugs) or senescence. We refer to the kinesin molecule, formed by the association of the Khcs protein with kinesin light chains, as kinesin-S, to distinguish it from the other kinesins present in mammalian cells. These results demonstrate that chemotherapeutic drug selection for GSEs can lead to the discovery of novel genetic elements, and can also reveal roles of genes in drug sensitivity that had never before been suspected.

EXAMPLE 6

Cloning and Analysis of the Gene From Which Anti-khcs GSE Gene was Derived

The anti-khcs GSE isolated in Example 4 was used as a probe to screen 400,000 clones from each of the two cDNA libraries in the lambda gt10 vector. These libraries were prepared by conventional procedures from the RNA of mouse BALB/c 3T3 cells, either unsynchronized or at B0→G1 transition, as described by Lan and Nathans, EMBO J. 4:3145–3151 (1985) and Proc. Natl. Acad. Sci. USA 84:1182–1186 (1987) (a gift of Dr. L. Lau). Screening of the first library yielded no hybridizing clones, but two different clones from the second library were found to contain anti-khcs sequences. These clones were purified and sequenced. Sequence analysis showed that we have isolated the bulk of the mouse khcs cDNA, corresponding to 796 codons (the full-length human KHC cDNA encodes 963 amino acids). This sequence is shown in FIGS. 12A through 12C. The missing 5' and 3' terminal sequences are currently being isolated using the "anchored PCR" technique, as described by Ohara et al., Proc. Natl. Acad. Sci. USA 86:5673–5677 (1989).

The dot-matrix alignment of the sequenced portion of the khcs protein with previously cloned KHC proteins from the human (see Navone et al., J. Cell. Biol. 117:1263–1275 (1992)), mouse (see Kato, J. Neurosci. 2:704–711 (1991) and squid (see Kosik et al., J. Biol. Chem. 265:3278–3283 (1990)) is shown in FIGS. 13A through 13D. The portion corresponding to the anti-khcs GSE, is shown in FIG. 9. The khcs gene is most highly homologous to the human gene (97% amino acid identity), suggesting that the human KHC (KHCS) gene is functionally equivalent to the mouse khcs. The alignment also shows that the anti-khcs GSE corresponds to the region which is the most highly diverged between different kinesins. This result suggests that the anti-khcs GSE is an antisense-oriented GSE fragment with an inhibitory effect specific to kinesin-S and not to the other mouse kinesins. This suggests the possibility that suppression of the other members of the kinesin family would have a detrimental effect on cell growth, the resulting in selective isolation of the most specific sequence within the khcs gene.

EXAMPLE 7

Assessment of Drug Cross-Resistance Conferred by Resistance to Etoposide

To determine the spectrum of drugs to which the anti-khcs GSE would confer resistance, we have developed a stable population of ecotropic packaging cells producing the LNCX virus with the anti-khcs insert. This virus was used to infect NIH 3T3 cells. Two days after infection, the cells were analyzed for resistance to several different drugs, relative to control cells infected with the LNCX vector virus, using the standard plating efficiency assay. FIGS. 14A through 14F shows one out of three sets of experiments carried out with different drugs by this assay. Cells infected with the anti-khcs virus showed a clear increase in their resistance to etoposide and Adriamycin relative to control NIH 3T3 cells infected with the control LNCX virus. No changes in resistance were observed with colchicine, cisplatin, camptothecin, or actinomycin D. These latter results remain preliminary, however, because this assay, analyzing total unselected virus-infected populations is relatively insensitive, compared with analysis of highly expressing individually-selected clones. Overall, these results demonstrate that selection of GSEs that confer resistance to one chemotherapeutic drug can result in obtaining GSEs that confer resistance to additional chemotherapeutic drugs.

EXAMPLE 8

Assessment of Cellular Effects of GSEs that Confer Resistance to Etoposide

The virus carrying the anti-khcs GSE was tested for the ability to increase the life span of primary mouse embryo fibroblasts (MEF). MEF were prepared from 10 day old mouse embryos by a standard trypsinization procedure and senescent cells were frozen at different passages prior to crisis. Senescent MEF, two weeks before crisis, were infected with recombinant retroviruses carrying LNCX vector either without an insert or with anti-khcs. FIG. 15 shows MEF cell colonies two weeks after crisis. Relative to uninfected MEF cells, or cells infected with a control LNCX virus, cell infected with anti-khcs showed a great increase in the proportion of cells surviving the crisis. Post-crisis cells infected with the anti-khcs virus showed no microscopically visible features of neoplastic transformation. These results indicate that anti-khcs promotes the immortalization of normal senescent fibroblasts. These results suggest that the normal function of kinesin-S may be associated with the induction of programmed cell death occurring after exposure to certain cytotoxic drugs or in the course of cellular senscence. These results also indicate that isolation of GSEs that confer resistance to chemotherapeutic drugs can provide insight into the cellular genes and processes involved in cell growth regulation.

EXAMPLE 9

Assessment of the Role of Decreased khcs Gene Expression in Naturally Occurring Mechanisms of Drug Resistance To test whether decreased khcs gene expression is associated with any naturally occurring mechanisms of drug resistance, an assay was developed for measuring khcs mRNA levels by cDNA-PCR. This assay is a modification of the quantitative assay described by Noonan et al., Proc. Natl. Acad. Sci. USA 87:7160–7164 (1990) for determining mdr-1 gene expression. The oligonucleotide primers had the sequences AGTGGCTGGAAAACGAGCTA [SEQ. ID. No. 19] and CTTGATCCCTTCTGGTTGAT [SEQ. ID. No. 20]. These primers were used to amplify a 327 bp segment of mouse khcs cDNA, corresponding to the anti-khcs GSE. These primers efficiently amplified the mouse cDNA template but not the genomic DNA, indicating that they spanned at least one intron in the genomic DNA. Using these primers, we determined that khcs mRNA is expressed at a higher level in the mouse muscle tissue than in the kidney, liver, or spleen.

Figure 16:
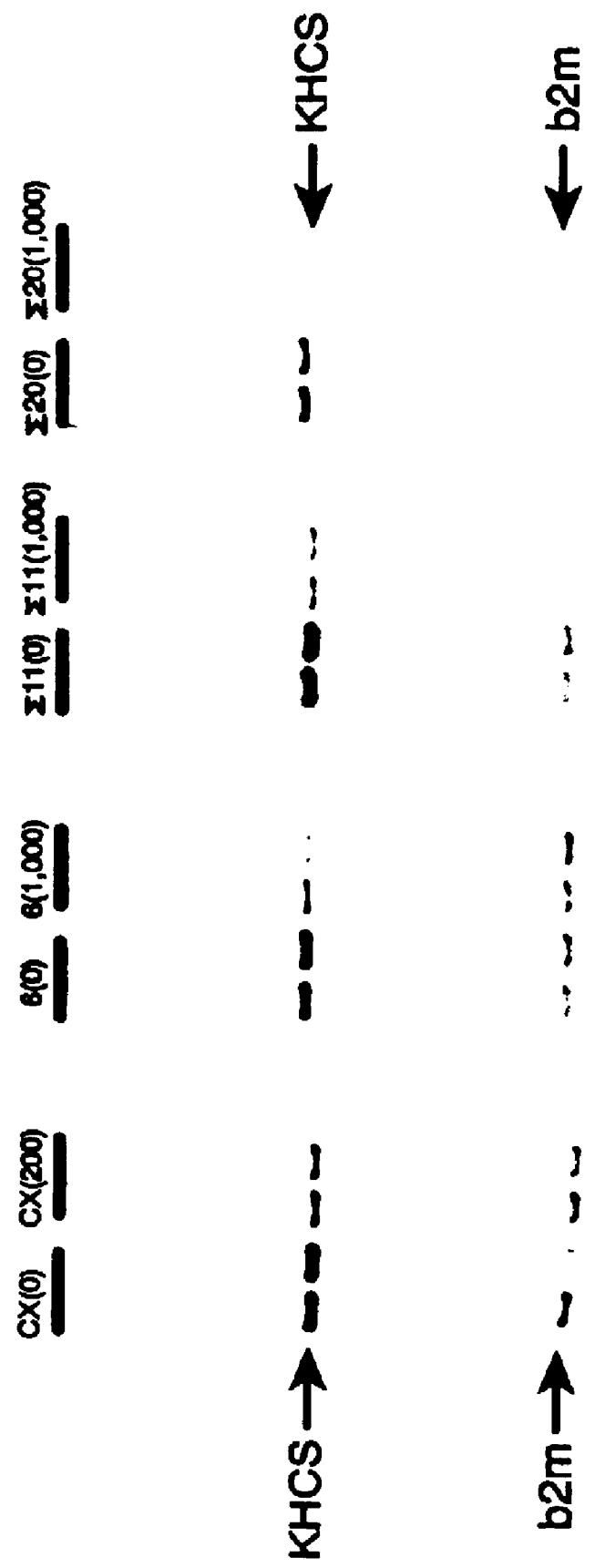
FIG. 16 shows cDNR-PCR quantitative analysis of expression of the human khcs gene in various unselected and etoposide-selected human HeLa cells. Lanes a show results for clone CX(O), lands a' for clone CX(200), lanes b and c for clone Σ11(O), lanes b' for clone Σ11 (1000), lanes c for clones 6(O), lanes c' for clone 6(1000), lanes d for clone Σ20(O) and lanes d' for clone Σ20 (1000). The numbers in parentheses for each clone name indicate the concentration of etoposide (ng/ml) present in the growth media. Bands indicative of khcs expression are shown along with bands for β-2 microglobulin expression as an internal control.

In another experiment a pair of primers amplifying a homologous segment of the human KHCS cDNA was selected, based on the reported human KHC sequence published by Navone et al., J. Cell. Biol. 117:1263–1275 (1992). The sequences of these primers are AGTGGCTTGAAAAT-GAGCTC [SEQ. ID. No. 21] and CTTGATCCCTTCTGG-TAGATG [SEQ. ID. No. 22], and they amplify a 327 bp cDNA fragment. These primers were used to test for changes in the KHCS gene expression in several independently isolated populations of human HeLa cells, each selected for spontaneously acquired etoposide resistance. $\beta_2$-microglobulin cDNA sequences were amplified as an internal control. FIG. 16 shows the results of the cDNA-PCR assay on the following populations: CK(0), HeLa population infected with the LNCX vector virus and selected with G418; CS (200), the same cells selected for resistance to 200 ng/ml etoposide; $\Sigma 11(0)$, $6(0)$ and $\Sigma 21(0)$, populations obtained after infection of HeLa cells with recombinant retroviruses carrying different GSEs derived from topoisomerase α cDNA, as described in Example 1, and selected with G418; $\Sigma 11(1000)$, $6(1000)$ and $\Sigma 21(1000)$, the same populations selected for resistance to 1 μg/ml etoposide. As shown in FIG. 16, the yield of the PCR product specific for the khcs gene was significantly lower in each of the etoposide-selected populations than in the controlled cells. This result indicates that a decrease in the khcs gene expression is a common natural mechanism for drug resistance.

What is claimed is:

1. A synthetic peptide having an amino acid sequence comprising from about 6 amino acids to all of the amino acids encoded by a genetic suppressor element identified by Seq. ID No. 2–5, 9, 11, 12, 16 or 17.

2. A synthetic peptide having an amino acid sequence corresponding to from about amino acids to all of the amino acids encoding a genetic suppressor element that is produced according to a method for identifying genetic suppressor elements that confer a selectable phenotype upon a eukaryotic cell, wherein the method comprises the steps of:

(a) synthesizing randomly fragmented cDNA prepared from the total mRNA of a cell to yield DNA fragments;

(b) transferring the DNA fragments to an expression vector to yield a genetic suppressor element library, wherein each of the DNA fragments is operatively linked to a protein translation initiation codon, and wherein the expression vector expresses the DNA fragments in a living eukaryotic cell that is capable of exhibiting the selectable phenotype;

(c) genetically modifying living cells by introducing the genetic suppressor element library into the living eukaryotic cells;

(d) isolating or enriching for genetically modified living eukaryotic cells containing genetic suppressor elements that confer the selectable phenotype by selecting cells that express the selectable phenotype;

(e) obtaining the genetic suppressor element from the genetically modified cells; and (f) identifying sense-oriented genetic suppressor elements therein, wherein the GSE comprises a portion of a nucleic acid selected from the group consisting of nucleic acids identified by Seq. ID Nos. 2–5, 9, 11, 12, 16 or 17, wherein said peptide disrupts an activity of a protein produced by the cell.

* * * * *

UNITED STATES PATENT AND TRADEMARK OFFICE
CERTIFICATE OF CORRECTION

PATENT NO. : 6,982,313 B2 Page 1 of 1
APPLICATION NO. : 10/010167
DATED : January 3, 2006
INVENTOR(S) : Roninson et al.

It is certified that error appears in the above-identified patent and that said Letters Patent is hereby corrected as shown below:

Col. 17, In SEQ ID NO: 2:, item (iv), please delete " yes " and substitute -- no --

Col. 19, In SEQ ID NO: 3:, item (iv), please delete " yes " and substitute -- no --

Col. 19, In SEQ ID NO: 4:, item (iv), please delete " yes " and substitute -- no --

Col. 19, In SEQ ID NO: 5:, item (iv), please delete " yes " and substitute -- no --

Col. 23, In SEQ ID NO: 9:, item (iv), please delete " yes " and substitute -- no --

Col. 23, In SEQ ID NO: 11:, item (iv), please delete " yes " and substitute -- no --

Col. 25, In SEQ ID NO: 12:, item (iv), please delete " yes " and substitute -- no --

Col. 27, In SEQ ID NO: 18:, item (iv), please delete " yes " and substitute -- no --

In Column 31, line 64, after " about " please insert -- 6 --

Signed and Sealed this

Twenty-second Day of August, 2006

JON W. DUDAS
*Director of the United States Patent and Trademark Office*